United States Patent
Aboagye et al.

(10) Patent No.: US 10,821,194 B2
(45) Date of Patent: *Nov. 3, 2020

(54) LABELLED CARBOXYLIC ACIDS AND THEIR USES IN MOLECULAR IMAGING

(71) Applicant: Cancer Research Technologies Limited, London (GB)

(72) Inventors: Eric O. Aboagye, London (GB); Lisa Iddon, London (GB); Federica Pisaneschi, London (GB); Timothy H. Witney, London (GB)

(73) Assignee: Cancer Research Technologies Limited, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 16/281,781

(22) Filed: Feb. 21, 2019

(65) Prior Publication Data

US 2019/0184039 A1    Jun. 20, 2019

Related U.S. Application Data

(62) Division of application No. 14/889,558, filed as application No. PCT/GB2014/051405 on May 8, 2014, now Pat. No. 10,213,516.

(30) Foreign Application Priority Data

May 8, 2013 (GB) .................................. 1308278.9

(51) Int. Cl.
*A61K 51/04* (2006.01)
*C07B 59/00* (2006.01)
*C07C 51/09* (2006.01)
*C07C 53/21* (2006.01)

(52) U.S. Cl.
CPC ........ *A61K 51/0402* (2013.01); *C07B 59/001* (2013.01); *C07C 51/09* (2013.01); *C07C 53/21* (2013.01)

(58) Field of Classification Search
CPC ...... A61K 51/0402; C07C 53/21; C07C 51/09
See application file for complete search history.

(56) References Cited

FOREIGN PATENT DOCUMENTS

WO    2012/012307 A1    1/2012

OTHER PUBLICATIONS

Winstead J. Nucl. Med., 1973, 14(10), p. 747-54. (Year: 1973).*
Karabatsos, JACS, 1961, 83, p. 1230-2. (Year: 1961).*
Examination Report, dated Sep. 25, 2019, issued in corresponding European Patent Application No. 14723857.0.

* cited by examiner

*Primary Examiner* — Michael G. Hartley
*Assistant Examiner* — Leah H Schlientz
(74) *Attorney, Agent, or Firm* — Kathleen D. Rigaut; Howson & Howson LLP

(57) ABSTRACT

The present invention pertains generally to the field of imaging compounds, and more specifically to certain 2,2-dialkyl radionuclide-labelled carboxylic acids suitable for PET, SPECT and/or DNP imaging. Also described are used of such compounds in the imaging of inter alia, cancer tumours, metastasis, Alzheimer's disease and multiple sclerosis.

27 Claims, 10 Drawing Sheets

LABELLED CARBOXYLIC ACIDS AND THEIR USES IN MOLECULAR IMAGING

CROSS-REFERENCE TO RELATED APPLICATIONS

This application is a divisional application of U.S. application Ser. No. 14/889,558, filed Nov. 6, 2015, which is a § 371 of International Application No. PCT/GB2014/051405, filed May 8, 2014, which claims priority to Great Britain Patent Application No. 1308278.9, filed May 8, 2013. The entire disclosure of each of the aforesaid applications is incorporated by reference in the present application.

FIELD OF THE INVENTION

The present invention relates to labelled carboxylic acids and their use in molecular imaging, and in particular to radionuclide-labelled carboxylic acids that do not bear a hydrogen at the carbon alpha to the carbonyl group, and to 2,2-dialkyl substituted carboxylic acids having a label suitable for hyperpolarisation.

BACKGROUND OF THE INVENTION

Positron emission tomography (PET) is routinely used in the clinic for cancer detection, with the majority of all scans performed with the glucose analogue [$^{18}$F]2-fluoro-2-deoxyglucose, [$^{18}$F]FDG. A number of clinical studies, however, have shown poor sensitivity for the detection of certain cancers, for example, prostate cancer, by [$^{18}$F]FDG-PET. Prostate cancer is the most prevalent of cancers in the male population, accounting for 40,841 incidents in the UK in 2009.[1] In the USA prostate cancer is the second largest cause of cancer mortality amongst men. The poor sensitivity for prostate cancer detection by [$^{18}$F]FDG-PET is thought to be a result of low basal glucose metabolism of some prostate tumours[2] and the high renal clearance of [$^{18}$F]FDG, which can often mask tumour uptake.[3] As a result, other PET tracers have been developed for cancer imaging including as [$^{11}$C]choline, [$^{18}$F]choline and [$^{11}$C]acetate.

[$^{11}$C]Acetate was initially developed as a radiotracer to evaluate oxidative metabolism in the myocardium. Following entry into the cell, either by passive diffusion or membrane transport via the monocarboxylate transporters,[4] [$^{11}$C]acetate is converted to [$^{11}$C]acetyl-CoA by acetyl CoA synthetase before its rapid metabolism via the citric acid cycle to [$^{11}$C]CO$_2$.[5] As well as being a substrate for the citric acid cycle, acetyl-CoA also enters into the fatty acid synthesis pathway, with tumour-associated [$^{11}$C]acetate accumulation shown to result from cell membrane incorporation following flux through the fatty acid synthesis pathway.

Experiments carried out by Yoshimoto and co-workers showed that [1-$^{11}$C]acetate was incorporated into the lipid soluble traction, mostly as phosphatidylcholine and neutral lipids. The accumulation of [1-$^{14}$C]acetate was positively correlated with the growth of the tumour cells. Fatty acid synthase (FAS) has been shown to be overexpressed in cancer, accounting for the uptake of acetate into the fatty acid synthesis pathway and incorporation into the cell membrane.[6,7] [$^{11}$C]Acetate has shown great promise in imaging prostate cancer, but the short half-life of carbon-11 (20.4 min) requires an on-site cyclotron, limiting its wide-spread use. [$^{18}$F]Fluoroacetate ([$^{18}$F]FAC, 1) has been investigated as an alternative to [$^{11}$C]acetate for imaging of prostate cancer. The radiotracer was introduced by Welch and co-workers.[8] The advantage of using fluorine-18 is its longer half-life of 109.5 min compared to the carbon-11 half-life of 20.4 min.

The authors in reference 8 investigated the biodistribution of [$^{11}$C]acetate and [$^{18}$F]FAC (1) in Sprague-Dawley rats. They found fairly rapid clearance of [$^{11}$C]acetate from most of organs except the pancreas at 1 h, whereas [$^{18}$F]FAC clearance was slower from most organs. This is thought to be due the oxidative metabolism of [$^{11}$C]acetate, releasing [$^{11}$C]CO$_2$. The main drawback of [$^{18}$F]FAC is its substantial bone uptake, characteristic of radiotracer defluorination.[9] A comparison with [$^{11}$C]acetate did describe a sizeable amount of the injected dose of [$^{18}$F]FAC was taken up by bones in pigs and less pronounced in monkeys. This unwanted and massive defluorination in pigs results in unspecific intense skeletal activity and imaging during PET, showing this tracer's limitations for use in higher animals. [$^{18}$F]Fluoroacetate is not a functional analogue of [$^{11}$C]acetate in normal physiology.[9] There are a number of putative routes for defluorination (Scheme 1). Tecle and Casida, for example, found that incubation of [$^{13}$C]fluoroacetate with rat and mouse liver cytosol leads to formation of S-([$^{13}$C]carboxymethyl) glutathione (2) and fluoride ion indicating that the fluoride ion is displaced by the glutathione (GSH) via a nucleophilic attack. Once [$^{18}$F]FAC enters the citric acid cycle, it is converted into 2-fluorocitrate 3. The same authors,[10] together with other groups,[11,12] showed that (−)-erythro-2-fluorocitrate is both a substrate and an inhibitor for aconitase, the latter is responsible for defluorination. The mechanism of defluorination requires the conversion of 2-fluorocitrate 3 into fluoro-cis-aconitate, which undergoes addition of hydroxide and subsequent loss of fluoride to form 4-hydroxy-trans-aconitate 4. Compound 4 binds very tightly to the enzyme and it is responsible for the toxicity of fluoroacetate at pharmacological levels.

Scheme 1

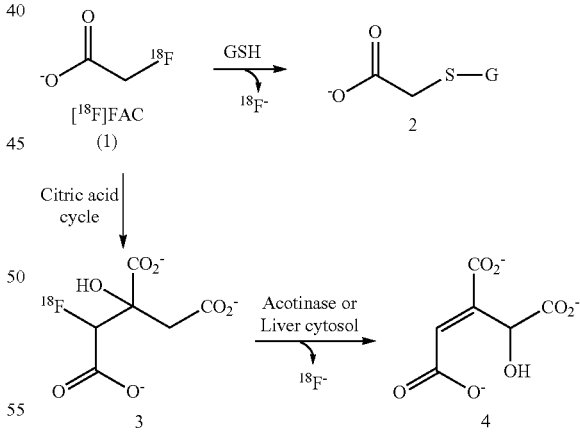

Given the inadequate performance of [$^{18}$F]FAC as a tracer that can be used to image biology of acetate metabolism preclinically in prostate cancer and beyond, there is an unmet need to provide a stable imaging agent which does not undergo de-labelling to lose its radionuclide label.

Dynamic nuclear polarization (DNP) of $^{13}$C-labeled molecules can increase their sensitivity of detection in a solution-state nuclear magnetic resonance experiment by >10,000 times.[13] This dramatic increase in sensitivity means that, after intravenous injection, the spatial distribution of the labelled molecule and its subsequent metabolism can be imaged in vivo using $^{13}$C magnetic resonance spectroscopic imaging (MRSI) techniques. Tracking metabolic reactions in vivo by DNP has been exemplified with hyperpolarised [1-$^{13}$C]pyruvate, whose metabolic products, [1-$^{13}$C]lactate, [1-$^{13}$C]alanine, and [$^{13}$C]bicarbonate, have been shown to correlate with disease progression and response to therapy.

In tumours, the metabolic fate of [1-$^{13}$C]pyruvate is label exchange to [1-$^{13}$C]lactate, catalysed by lactate dehydrogenase, the final enzyme in the glycolytic pathway. Since the pyruvate blood-brain barrier (BBB) is rate limited,[14] hyperpolarised [1-$^{13}$C]pyruvate may have limited utility for determining disease-state under conditions where an intact BBB is present, for example, infiltrating gliomas, Alzheimer's disease, nonenhancing multiple sclerosis, and acute stroke. Unsubstituted [1-$^{13}$C]propionate has previously been polarised to high levels by DNP, and its metabolic products imaged in vivo during ischemia.[15]

There exists a need to provide imaging agents for DNP that can measure disease-state in the brain. Moreover, a measure of metabolic flux in pathways other than glycolysis may provide alternate and complementary prognostic information for diseases in other tissues of the body.

SUMMARY OF THE INVENTION

Broadly, the present invention relates to compositions comprising novel tracers for use in molecular imaging, and to the use of these compositions as imaging agents in molecular imaging. In particular, the present invention is based on the inventors' insight that radionuclide-labelled carboxylic acids that are devoid of protons at the position alpha to the carbonyl group of the carboxylic acid may be useful as radiotracers that are resistant to the de-labelling pathways described above (Scheme 1) and the associated drawbacks, while still exhibiting the desired uptake profile. Additionally, the present invention is based on the insight that such compounds having a label suitable for polarization using dynamic nuclear polarisation (DNP) in addition to, or as an alternative to, a radionuclide label may be useful tracers for spectroscopic imaging.

The compositions of the present invention are generally applicable for molecular imaging of diseases and disorders using PET and/or SPECT (depending on the radionuclide chosen) and/or spectroscopic imaging by magnetic resonance spectroscopy (MRS) or magnetic resonance imaging (MRI) following polarisation of the molecule by dynamic nuclear polarisation (DNP) if a suitable isotope, for example, [$^{13}$C]carbon or [$^{15}$N]nitrogen, is included. Accordingly, compositions of the invention may be used, for example, for the imaging of tumours, metastasis and heart-related diseases and disorders. In particular, compositions of the present invention may have utility as tracers for the imaging of tumours which have a high fatty acid turnover and/or are hypoxic or for which [$^{18}$F]FDG imaging is sub-optimal.

Compositions of the present invention may be useful as tracers in the detection of acetyl-CoA synthetase (ACSS) activity in, for example, tumour cells. ACSS is expressed in 2 isoforms: ACSS1 & 2. Some tumour cells have a higher expression level of ACSS 1/2 than normal cells and hypoxia increases ACSS activity even more (also free fatty acids). Therefore, tissue of tumours of these types will be enriched for the tracers of the present invention.

Without wishing to be bound by any particular theory, the present inventors believe that ACSS1/2 activity results in the carboxylic acid moieties of the tracer compounds of the present invention being converted to the corresponding CoA adduct. Further oxidation to $CO_2$ is not possible in mammalian cells.

The present inventors have found that increased uptake of compounds of the invention may be observed following incubation with L-carnitine. As carnitine esters are known to be products of both [$^{13}$C]acetate and [$^{13}$C]propionate catabolism in the heart, without wishing to be bound by any particular theory, the inventors believe that the mechanism of trapping of compounds of the invention may occur via CoA and carnitine ester formation. Transesterification of CoA adduct to a carnitine ester occurs under the action of carnitine acyl transferases.[25] The carnitine adduct is membrane impermeable and may be transported out of tissues via the human kidney carnitine transporter (hOCTN2), whose transport is competitively inhibited by L-carnitine.[26] Uptake may work via two different mechanisms: diffusion or possibly by facilitated diffusion. In addition to ACSS activity, compositions of the present invention may be useful as tracers in the detection of cartinie acetyltransferase activity and/or activity of the facilitated diffusion transporter in, for example, tumour cells.

In a first aspect, the present invention relates to compositions comprising a tracer, wherein the tracer is a labelled carboxylic acid, or the corresponding carboxylate anion thereof, that does not bear a hydrogen at its alpha carbon. These compounds are able to form the desired CoA- and carnitine adducts but, owing to the absence of alpha protons, are not metabolised and are therefore more stable than, for example, [$^{18}$F]FAC. The labeled carboxylic acids described herein are short alkyl chain carboxylic acids, for example, 2,2-disubstituted-acetic, -propanoic, -butanoic or -pentanoic acids. It will be appreciated that, as described herein, these acidic backbones may be substituted in addition to being labelled.

Accordingly, described herein are radionuclide-labelled carboxylic acids that are compounds of formula (I):

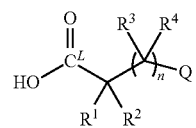

(I)

wherein Q is a suitable radionuclide; $C^L$ is [$^{11}$C], [$^{12}$C], or [$^{13}$C], optionally $C^L$ is [$^{12}$C] or [$^{13}$C], preferably [$^{12}$C]; n may be 0, 1, 2, or 3, for example, n may be 0, 1, or 2, preferably 1 or 2; $R^1$ and $R^2$ are inductively electron-donating substituents; and $R^3$ and $R^4$ are independently H or F.

A value of n>0 may be advantageous and result in compounds of the invention that are even less reactive towards GSH due to the increased distance of the activating carboxylic acid/carboxylate group.

In a first aspect, the present invention provides a composition comprising a tracer, wherein the tracer is a labelled 2,2-di-$C_{1-4}$-alkylpropanoic acid, 2,2-di-$C_{1-4}$-alkylbutanoic acid, 2,2-di-$C_{1-4}$-alkylpentanoic acid, or the corresponding carboxylate, wherein the tracer is labelled with:
 a radionuclide and/or
 a label suitable for polarisation using dynamic nuclear polarisation (DNP).

Suitably, the tracer comprises a radionuclide. For example, the tracer may be a radionuclide-labelled carboxylic acid or the corresponding carboxylate, wherein the radionuclide-labelled carboxylic acid is a compound of formula (I):

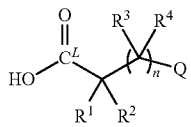

(I)

wherein
Q is a suitable radionuclide;
$C^L$ is selected from [$^{11}$C]carbon, [$^{12}$C]carbon or [$^{13}$C]carbon;
n is 1, 2, or 3;
$R^1$ and $R^2$ are independently $C_{1-4}$-alkyl; and
$R^3$ and $R^4$ are independently H or F.

Preferably, $R^3$ and $R^4$ are both hydrogen.
Preferably, n is 1 or 2, more preferably, n is 1.
In preferred compounds, $R^1$ and $R^2$ are both methyl.
In preferred compounds of the invention, $R^1$ and $R^2$ are both methyl, n is 1, and $R^3$ and $R^4$ are both H.

Suitable radionuclides are known in the art and include [$^{11}$C]carbon, [$^{18}$F]fluorine, [$^{13}$N]nitrogen, [$^{15}$O]oxygen, [$^{76}$Br]bromine, [$^{123}$I]iodine, [$^{124}$I]iodine, and [$^{125}$I]iodine. An especially preferred radionuclide is [$^{18}$F]fluorine.

$C^L$ is a carbon isotope selected from [$^{11}$C]carbon, [$^{12}$C]carbon and [$^{13}$C]carbon. In some embodiments, $C^L$ may be selected from [$^{12}$C]carbon or [$^{13}$C]carbon. For example, $C^L$ may be [$^{12}$C]carbon. In other embodiments, $C^L$ may be [$^{13}$C]carbon. In these cases, the [$^{13}$C]carbon is a label suitable for hyperpolarisation using DNP.

The tracer may be a labelled carboxylic acid or the corresponding carboxylate of formula (Ia):

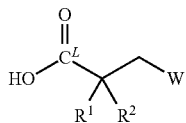

wherein:
$R^1$ and $R^2$ are $C_{1-4}$alkyl;
$C^L$ is [$^{11}$C]carbon, [$^{12}$C]carbon, or [$^{13}$C]carbon;
W is $R^5$ or Q;
$R^5$ is H, F, Cl, Br, I, or $NH_2$; and
Q is a radionuclide.

In some embodiments, W is Q. In other embodiments, W is $R^5$.
In preferred compounds, $R^1$ and $R^2$ are both methyl.
In some embodiments, the tracer is a [1-$^{13}$C]2,2-dimethylpropanoic acid, wherein the three position is substituted with F, [$^{18}$F]F, Cl, Br, [$^{76}$Br]Br, I, [$^{123}$I]I, [$^{124}$I]I, [$^{125}$I]I, or $NH_2$, optionally with F, [$^{18}$F]F, Cl, Br, [$^{76}$Br]Br, [$^{123}$I]I, [$^{124}$I]I, or [$^{125}$I]I.

In preferred compounds of the invention, $R^1$ and $R^2$ are both methyl, n is 1, and $R^3$ and $R^4$ are both H. In some preferred embodiments, the compound is selected from:
[$^{18}$F]3-fluoro-2,2-dimethylpropanoic acid, referred to herein as [$^{18}$F]FDMP and as [$^{18}$F]FPIA;
[1-$^{13}$C][$^{18}$F]3-fluoro-2,2-dimethylpropanoic acid, referred to herein as [1-$^{13}$C][$^{18}$F]FDMP and as [1-$^{13}$C][$^{18}$F]FPIA; and
[1-$^{13}$C]3-fluoro-2,2-dimethylpropanonic acid, referred to herein as [1-$^{13}$C]FDMP and as [1-$^{13}$C]FPIA.

In a further aspect, the present invention provides use of compositions of the present invention as imaging agents. Compositions comprising tracers labelled with radionuclides as described herein are suitable for imaging techniques that detect gamma rays.

In a further aspect, the present invention provides compositions of the present invention for use in a method of imaging for diagnosing a condition in a subject, wherein the method comprises:
(i) administering the composition to the subject;
(ii) detecting gamma rays emitted, either directly or indirectly, by the tracer;
(iii) acquiring at least one image associated with the gamma rays emitted by the tracer; and
(iv) diagnosing the condition in the subject using the image.

In some methods of the present invention, the composition may be pre-administered. Accordingly, in a further aspect, the present invention provides compositions according to the present invention for use in a method of imaging for diagnosing a condition in a subject, wherein the subject has been pre-administered with a composition according to the present invention, wherein the method comprises:
(i) detecting gamma rays emitted, either directly or indirectly, by the tracer;
(ii) acquiring at least one image associated with the gamma rays emitted by the tracer; and
(iii) diagnosing the condition in the subject using the image.

In a further aspect, the present invention provides methods for imaging a condition in a subject using a composition according to the present invention, the methods comprising the steps of:
(i) administering a composition comprising a tracer according to the present invention to the subject;
(ii) detecting gamma rays emitted by the tracer; and
(iii) acquiring at least one image associated with the gamma rays emitted by the tracer.

The method may then further comprise the step(s) of diagnosing the condition in the subject using the image and/or comparing the image with a previously obtained image to monitor progression of the condition and/or response to therapy.

In a further aspect, the present invention provides methods for detecting a condition in a subject using compositions according to the present invention, the subject having been pre-administered with a composition according to the present invention, the methods comprising the steps of:
(i) detecting gamma rays emitted, either directly or indirectly, by the tracer; and
(ii) evaluating the condition based on the detection of the gamma rays emitted by the tracer.

Also described herein are compositions comprising a tracer suitable for spectroscopic imaging by MRS or MRI following polarisation of the molecule by DNP, wherein the tracer is a carboxylic acid or the corresponding carboxylate that does not bear a hydrogen at its alpha carbon, the alpha carbon being substituted with at least two $C_{1-4}$alkyl substituents, wherein the tracer comprises a [$^{13}$C] or [$^{15}$N] label. In some embodiments, the carboxylic acid is a substituted propanoic acid, for example, [1$^{13}$C]-2,2-dimethylpropanoic acid. The three position may be optionally substituted with F, [$^{18}$F]F, Cl, Br, [$^{76}$Br]Br, [$^{123}$I]I, [$^{124}$I]I, or [$^{125}$I]I, preferably F or [$^{18}$F]F.

It will be appreciated that imaging may use one or more imaging techniques, for example, the imaging may be PET/SPECT, PET/SPECT and DNP or DNP alone.

Accordingly, the present invention further provides a composition comprising a tracer, wherein the tracer is a labelled 2,2-di-$C_{1-4}$-alkylpropanoic acid, or the corresponding carboxylate, wherein the tracer is labelled with a radionuclide and/or a label suitable for polarisation using dynamic nuclear polarisation (DNP), wherein the tracer is a labelled carboxylic acid or the corresponding carboxylate of formula (Ia):

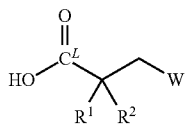

wherein:

$R^1$ and $R^2$ are $C_{1-4}$alkyl;

$C^L$ is [$^{11}$C]carbon, [$^{12}$C]carbon, or [$^{13}$C]carbon;

W is $R^5$ or Q;

$R^5$ is H, F, Cl, Br, I, $NH_2$; and

Q is a radionuclide.

In some embodiments, $C^L$ is [$^{13}$C]carbon.

Accordingly, in a further aspect, the present invention provides a composition comprising a tracer suitable for MRS or MRI following polarisation of the molecule by DNP for use in a method of imaging for diagnosing a condition in a subject, wherein the method comprises:

(i) hyperpolarising the tracer compound by DNP;

(ii) administering the composition to the subject;

(iii) collecting MRS or MRI data associated with the hyperpolarized tracer compound;

(iv) acquiring at least one image by MRS or MRI; and (v) diagnosing the condition in the subject using the image.

In yet a further aspect the present invention provides compositions comprising a tracer suitable for spectroscopic imaging by MRS or MRI following polarisation of the molecule by DNP for use in a method of imaging for diagnosing a condition in a subject, wherein the subject has been pre-administered with a composition, the composition having been hyperpolarised by DNP, wherein the method comprises:

(i) collecting MRS or MRI data associated with the hyperpolarized tracer compound;

(ii) acquiring at least one image by MRS or MRI; and (iii) diagnosing the condition in the subject using the image.

In any of the imaging methods of the invention, a second imaging technique or step may be used, and for compounds of the invention comprising both a radionuclide and a label suitable for hyperpolarisation, a combination of PET and/or SPECT with MRS or MRI following hyperpolarision of the tracer compound by DNP. In any of the imaging methods of the invention, the subject may be human or animal.

In a further aspect the present invention provides a method of synthesising a composition comprising a compound of formula (II)

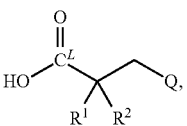

the method comprising the step of treating a compound of formula (III)

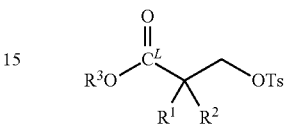

with a reagent comprising a radionuclide nucleophile to give a compound of formula (IV)

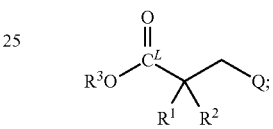

wherein Q is a radionuclide or group comprising a radionuclide; $C^L$ is selected from [$^{12}$C]carbon or [$^{13}$C]carbon, preferably [$^{12}$C]carbon; and $R^1$, $R^2$ and $R^3$ are independently $C_{1-4}$alkyl.

In a further aspect, the present invention provides a kit for the preparation of a radionuclide-labelled imaging agent, the kit comprising a compound of formula (III) and instructions for a method according to the present invention.

Embodiments of the present invention will now be described by way of example and not limitation with reference to the accompanying figures. However various further aspects and embodiments of the present invention will be apparent to those skilled in the art in view of the present disclosure.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

DETAILED DESCRIPTION

Tracers

Figure 1:
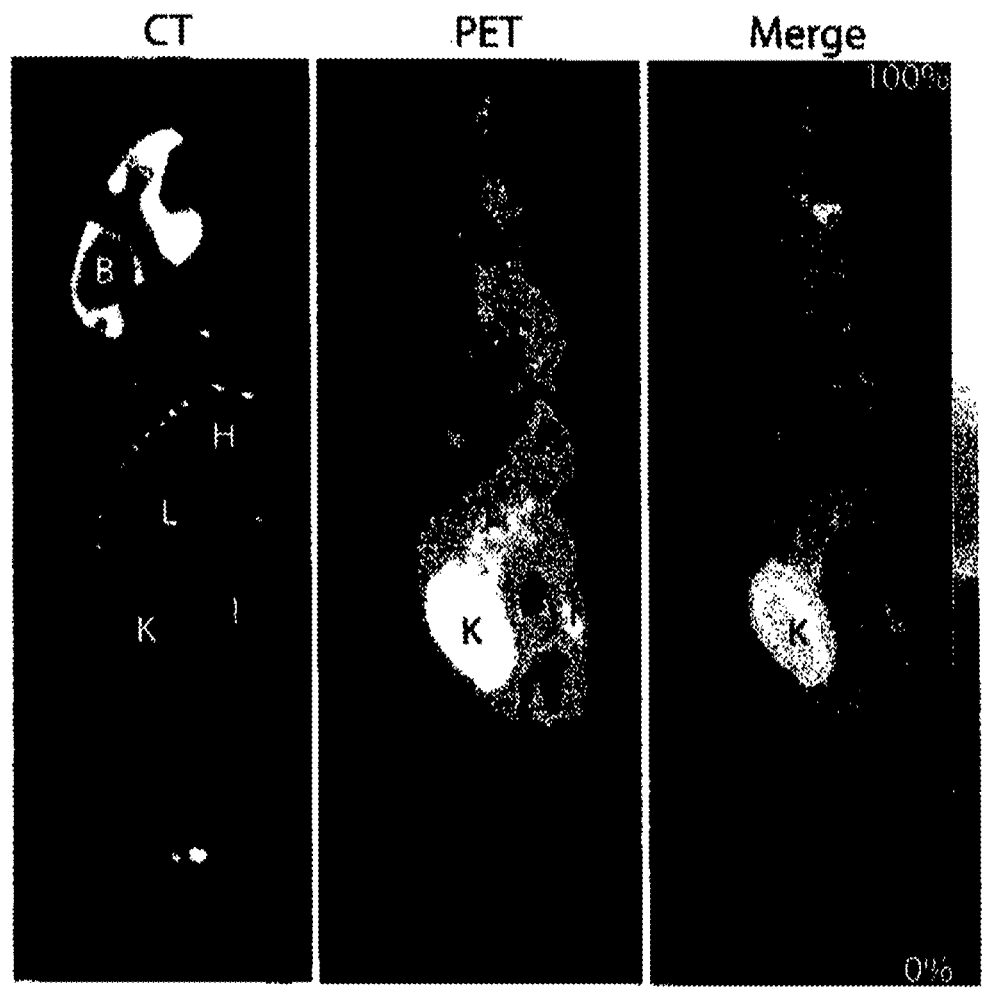
FIG. 1. PET imaging with [$^{18}$F]FDMP in healthy BALB/c mice. Representative sagittal CT (left), PET (middle), and PET-CT (right) images (30-60 min summed-activity) for [$^{18}$F]FDMP. Key organs are identified. Abbreviations: B, brain; H, heart; L, liver: K, kidney; I, intestines.

At their most general, the tracer compounds of the invention are labelled carboxylic acids that do not bear a hydrogen at the position alpha to the carboxylic acid carbonyl, that is, at the 2 position. Accordingly, compounds of the invention are labelled 2,2-disubstituted carboxylic acids, wherein the two 2-substitutents may be referred to as $R^1$ and $R^2$. The carboxylic acids of the invention are short alkyl chain (e.g. $C_{3-5}$) carboxylic acids, for example and not by way of limitation, 2,2-disubstituted propanoic, butanoic or pentanoic acids.

It will be understood that the carboxylic acid moieties of compounds of the present invention will be prone to deprotonation and all references to carboxylic acid compounds herein include the corresponding carboxylate anion.

Preferred substituents include inductively electron-donating substituents, for example, $C_{1-4}$alkyl substituents, wherein the $C_{1-4}$alkyl may be linear or branched, and saturated or unsaturated. Examples of suitable $C_{1-4}$alkyl substituents may include, but are not limited to, methyl, ethyl, vinyl, n-propyl, i-propyl, allyl, n-butyl, i-butyl, s-butyl, and t-butyl. For example, in some embodiments, $R^1$ and $R^2$ are selected from the following combinations:

| $R^1$ | $R^2$ |
|---|---|
| Me | Me |
| Me | tBu |
| nBu | tBu |
| Me | iPr |
| Et | nBu |
| Me | Allyl |
| nBu | nBu |
| iBu | Allyl |

Described herein are tracer compounds of formula (I):

In compounds of formula (I), Q is a label, preferably a radionuclide suitable for use in PET or SPECT methods. Details of suitable labels for use in PET or SPECT methods are provided below. In compounds of formula (I), n may be 0, 1, 2, or 3, preferably 1, 2, or 3, more preferably 1 or 2, especially preferably 1.

In compounds of formula (I), $R^1$ and $R^2$ are inductively electron-donating substituents, preferably alkyl groups as detailed above, more preferably methyl groups.

In compounds of formula (I), $R^3$ and $R^4$ are independently hydrogen or fluoride, preferably hydrogen.

Optionally, a carbon isotope other than the most naturally-abundant carbon isotope, [$^{12}$C]carbon, may be incorporated at 1-C. For example, incorporation of a [$^{13}$C]carbon at 1-C.

In some preferred embodiments, the tracer compounds of the present invention are labelled 2,2-disubstituted short alkyl chain carboxylic acids, for example, propanoic acids, wherein the two 2-substituents are $C_{1-4}$alkyl. In some embodiments, the compounds are compounds of formula (Ia) comprising a radionuclide and/or a label suitable for imaging by MRS or MRI following hyperpolarization by DNP.

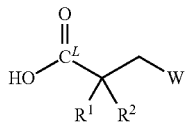

(Ia)

wherein $R^1$ and $R^2$ are $C_{1-4}$alkyl; $C^L$ is [$^{12}$C]carbon, [$^{11}$C]carbon, or [$^{13}$C]carbon; and W is $R^5$ or Q, wherein $R^5$ is H, F, Cl, Br, I, or $NH_2$, preferably H or F, and Q is a radiolabel as defined herein.

In some embodiments, $C^L$ is [$^{12}$C]carbon and W is Q.

In some preferred compounds of the invention both of the 2-substituents are methyl, that is, the compounds are compounds of formula Ib:

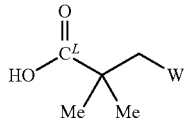

(Ib)

wherein $C^L$ and W are as defined herein, and the compounds comprise a radionuclide and/or a label suitable for imaging by MRS or MRI following hyperpolarization by DNP.

The tracer compounds of the present invention comprise a label that is an isotope suitable for detection in medical imaging techniques. In some embodiments, the compounds comprise a radionuclide suitable for detection PET and/or SPECT imaging techniques. Suitable radionuclides for PET are known in the art and include, but are not limited to, [$^{11}$C]carbon, [$^{13}$N]nitrogen, [$^{15}$O]oxygen, [$^{18}$F]fluorine, [$^{76}$Br]bromine, and [$^{124}$I]iodine. Suitable radionuclides for SPECT are known in the art and include [$^{123}$I]iodine, and [$^{125}$I]iodine. Accordingly, in some embodiments of the present invention, the radionuclide is selected from [$^{11}$C]carbon, [$^{13}$N]nitrogen, [$^{15}$O]oxygen, [$^{18}$F]fluorine, [$^{76}$Br]bromine, [$^{123}$I]iodine, [$^{124}$I]iodine, and [$^{125}$I]iodine. In some embodiments, the radionuclide is selected for PET imaging and is selected from [$^{11}$C]carbon, [$^{13}$N]nitrogen, [$^{15}$O]oxygen, [$^{18}$F]fluorine, [$^{76}$Br]bromine, and [$^{124}$I]iodine. Preferably, the radionuclide is [$^{18}$F]fluorine. In some embodiments, the radionuclide is selected for SPECT imaging and is selected from [$^{123}$I]iodine and [$^{125}$I]iodine. Additionally or alternatively, the compounds may comprise a label suitable for hyperpolarisation, such that the compound may be used in DNP imaging methods. Suitable labels include [$^{13}$C] and [$^{15}$N]. It will be appreciated that where a label has additional valencies, these valencies are occupied by hydrogen radicals. For example, an [$^{15}$N] label is present as [$^{15}$N]H$_2$.

A particularly preferred compound is [$^{18}$F]3-fluoro-2,2-dimethylpropanoic acid, which may also be called [$^{18}$F]3-fluoro-2,2-dimethylpropionic acid and [$^{18}$F]3-fluoranyl-2,2-dimethylpropionic acid, and is also referred to herein as [$^{18}$F]FDMP and as [$^{18}$F]FPIA ([$^{18}$F]fluoropivalic acid).

Uses of the Present Invention

The tracer compounds of the present invention may be used for the molecular imaging of diseases, such as cancer, metastasis, inflammatory diseases such as multiple sclerosis (MS) and neurodegenerative diseases such as Alzheimer's disease, and heart-related diseases and disorders. The applications of the imaging tracers of the present invention include a wide range of imaging and spectroscopic applications that can employ the imaging tracer and/or a further label, for example, in multi-modal imaging studies. As described herein, radio-labelled tracers of the present invention are particularly useful for in vivo imaging applications such as PET and SPECT. This might be useful in a number of different medical or research applications, for example in the fields of cancer detection and characterisation, the monitoring of disease progression and treatment effects/outcomes, and in the detection and monitoring of heart-related diseases and disorders.

The present invention is particularly relevant to nuclear medicine imaging techniques, such as PET, an imaging technique that provides three-dimensional images by detecting pairs of gamma rays emitted indirectly by a positron-emitting radionuclide introduced into a sample or subject, and SPECT, an imaging technique that detects gamma rays emitted from a radionuclide to produce a three dimensional image of the distribution of the radionuclide in a sample or subject.

In some embodiments of the invention, the compounds comprise a $^{15}$N or $^{13}$C label for spectroscopic imaging by MRS or MRI following polarisation of the molecule by DNP. In preferred compounds, the label is $^{13}$C and is preferably at the C-1 position of the carboxylic acid lacking a hydrogen at its alpha carbon, that is, the compound may be, for example, a [1-$^{13}$C]-2,2-disubstituted propanoic acid such as [1-$^{13}$C]FDMP.

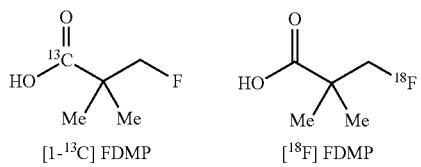 [SMILES: CC(C)(CF)[13C](=O)O ; CC(C)(C[18F])C(=O)O]

[1-$^{13}$C] FDMP     [$^{18}$F] FDMP

The tracers of the present invention may be used in methods of multi-modal imaging, that is where information or images are derived from two different techniques, either by the detection of the imaging tracer capable of detection using two different techniques as explained in detail herein or by providing a second label at the site in the biological system where the tracer becomes localised, most conveniently by linking or associating the second label with the tracer. Multi-modal studies will be co-registered and may entail simultaneous imaging with two modalities or may need to take place in two steps, but generally employ the same sample so that spatial information obtained using the two techniques can be compared. Accordingly, in some methods of the present invention a second imaging technique is used. Examples of multi-modal imaging include PET/CT, SPECT/CT, PET/MR and SPECT/MR.

[$^{18}$F]Fluorine labelled compounds of the invention may be especially as advantageous as, owing to the long half-life of [$^{18}$F]fluorine in combination with the enhanced stability to metabolism associated with compounds of the invention, these compounds may be especially useful in performing duel-case PET/CT imaging to distinguish between benign/reactive and malignant lymph nodes, for which type of imaging a stable tracer with a long half-life is needed.

It may be preferable to incorporate two labels into a compound of the present invention, for example, a radionuclide for detection using PET or SPECT, and a label suitable for spectroscopic imaging by MRS or MRI following polarisation of the molecule by DNP, such as a [$^{13}$C] carbon. Examples of suitable compounds could include, for example, [$^{18}$F][1-$^{13}$C]-2,2-disubstituted propanoic acids such as [$^{18}$F][1-$^{13}$C]FDMP. In methods using compound tracers of this type, the second imaging technique includes the step of hyperpolarising the molecule by DNP before obtaining the MRS or MRI.

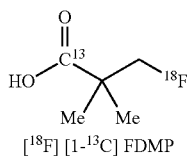

[$^{18}$F] [1-$^{13}$C] FDMP

Owing to their stability to metabolism, tracers of the invention may be useful for multimodal imaging with a time delay between imaging steps. For example, it may be useful to image the tracer at delayed time points to improve signal to noise contrast for the imaging of certain conditions and tumours, for example, metastasis. Accordingly, in some methods of the present invention, the method further comprises obtaining multiple data sets associated with imaging the tracer, these data sets being obtained at spaced time intervals of, for example, between about 30 min and 1 h. The compositions and methods of the present invention may further have utility in multimodal imaging techniques having a time delay between imaging sessions, for example in dual-case PET/CT techniques which feature two imaging sessions over a course of time.

The compositions and methods of the present invention may be used as imaging agents and may useful in a variety of clinical and pre-clinical settings. For example, the imaging compositions and methods of imaging of the present invention may be useful at the diagnosis stage and during treatment. Imaging may be used to detect the presence of, for example and not by way of limitation, a lesion, diseased tissue, a tumour, metastasis or a heart-related condition or disorder and/or to quantify the size or distribution of the lesion, diseased tissue, tumour, metastasis, a genetic/epigenetic disease of lipid metabolism, or heart-related condition or disorder such as heart disease. Examples of genetic/epigenetic diseases of lipid metabolism may include, but are not limited to, Gaucher disease, Tay-Sachs disease (also known as GM2 gangliosidosis or hexosaminidase A deficiency). Other inflammatory diseases can be detected, for example multiple sclerosis, in addition to neurodegenerative diseases, including Alzheimer's disease.

Methods of the present invention may be used to monitor a condition in a subject after diagnosis to determine and/or monitor disease progression, amelioration, shrinkage, response to treatment, for example, drug or radiation therapy, etc. and to detect any changes in, for example, tumour behaviour. Accordingly, in some embodiments, methods of imaging and methods of imaging for the purposes of diagnosing, evaluating or monitoring a condition may be repeated more than once to follow the progress of a condition and/or response to treatment such as drug or radiation therapy, over time.

In some methods of the present invention, the condition is a lesion or diseased tissue that has a high lipid metabolism compared to levels in healthy tissue of the same organ or origin, and may, for example, be a tumour having increased ACSS activity/expression, in particular, increased ACSS2 activity/expression, increased carnitine acetyltransferase activity/expression, and/or activity of the facilitated diffusion transporters. The tumour may be a hypoxic tumour and/or may be a benign tumour or a cancer tumour, for example, a tumour associated with breast, brain, prostate, colon, esophageal, lung, pancreatic or liver (including hepatocellular carcinoma HCC) cancer. In some methods of the present invention, the cancer is selected from breast, brain or prostate cancer. In some methods of the present invention, the tumour is a brain tumour.

Metabolic Stability and Relationship with Glucose Metabolism

Without wishing to be bound to any particular theory, the present inventors believe that the lack of protons alpha to the carbonyl in the labelled compounds of the invention prevents the compounds from entering the citric acid cycle. This is a particular disadvantage associated with the known PET tracer [$^{18}$F]FAC, which undergoes defluorination as described above. Consequently, [$^{18}$F]FAC performs inadequately as a tracer in the biological imaging of acetate metabolism preclinically in, for example, prostate cancer.

The scheme below shows the first step of the citrate synthase mechanism. The previously published mechanism for entry of acetate into the citric acid cycle[16] has been adapted to show the first step in this cycle for [$^{11}$C]acetate, [$^{18}$F]FAC and [$^{18}$F]3-fluoro-2,2-dimethylpropanoic acid [$^{18}$F]FDMP), which is a preferred compound of the present invention. The present inventors believe that the lack of a proton alpha to the carbonyl prevents Asp375 from attacking compounds of the invention, disabling the compounds from entering the citric acid cycle and losing the radionuclide label.

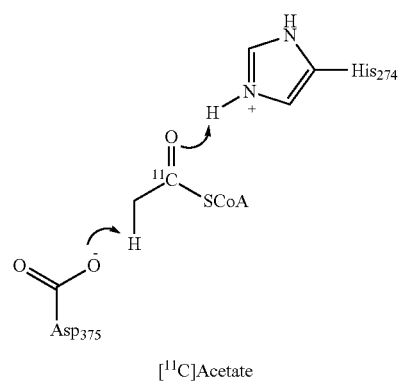

[$^{11}$C]Acetate

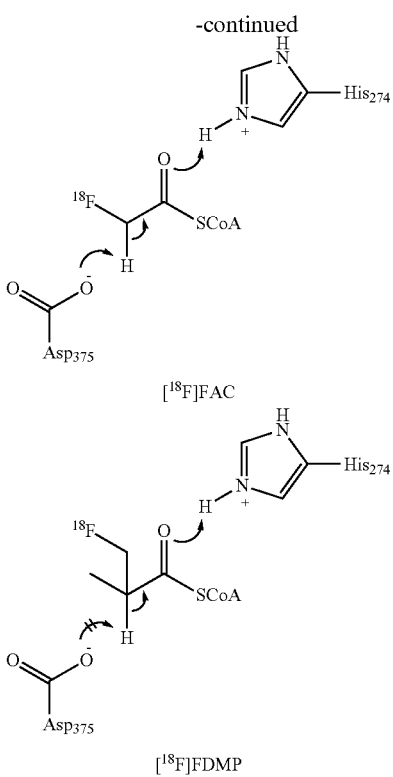

[<sup>18</sup>F]FAC

[<sup>18</sup>F]FDMP

In addition to the inability to participate in the citrate acid cycle, the labelled carboxylic acids of the invention may also be less reactive towards GSH, increasing stability and resistance to metabolism and, where present and applicable, loss of the radionuclide label.

Compounds of the invention have the potential to be converted into an acetyl-CoA derivative through reaction at the carboxylic acid moiety, resulting in the capacity to map the initial step of fatty acid metabolism. This is thought to be analogous to the use of [$^{18}$F]fluorodeoxyglucose [$^{18}$F]FDG) to map glucose metabolic flux by tumour cells. However, [$^{18}$F]FDG is known to discriminate poorly between healthy and diseased tissue where high glucose uptake/metabolism is a feature of the normal tissue. Compounds of the invention, by contrast, have been shown to demonstrate superior results in these tissues types (vide infra). Accordingly, in some methods of the present invention, the condition is a tumour located in a tissue-type having high levels glucose uptake/metabolism, for example a benign or cancerous brain tumour.

Steric bulk and inductive effects caused by the necessary alpha substituents may decrease susceptibility to reaction with GSH. In preferred compounds of the invention in which a radionuclide is located at a position beta or gamma, preferably beta, to the carbonyl of the carboxylic acid, the present inventors believe that these compounds may be less reactive towards GSH and de-labelling due to the increased distance of the activating carboxylic acid/carboxylate group. In especially preferred compounds of the invention, for example, 3-radionuclide-2,2-dimethyl propanoic acids, steric bulk, inductive effects and increased distance between the radionuclide and the carboxylic acid moiety in combination result in compounds particularly resistant to this reaction pathway.

[$^{18}$F]FDMP

[$^{18}$F]FDMP has been extensively investigated by the present inventors as a potential PET tracer for cancer imaging and inflammation imaging. Imaging in an inflammation model may be of use in the detection and imaging of non-malignant inflammation related pathologies such as Alzheimer's disease and multiple sclerosis.

[$^{18}$F]FDMP Uptake and Trapping

In EMT6 breast cancer cells [$^{18}$F]FDMP was converted to an unknown metabolite; the increased uptake of [$^{19}$F]FDMP following incubation with L-carnitine implicates this metabolite as a putative [$^{18}$F]FDMP CoA or carnitine-ester. Extensive work to synthesize the [$^{19}$F]FDMP CoA or carnitine ester reference material was unsuccessful. Using mass spectrometry, intracellular levels of [$^{18}$F]FDMP were confirmed but again the inventors were unable to rule out the existence of metabolites by comparison to [$^{19}$F]FAC. Supporting these data, carnitine-esters have previously been shown as the major metabolic products of both [$^{13}$C]acetate and [$^{13}$C]propionate catabolism in the heart, measured over a far shorter experimental window of 70 s by hyperpolarized $^{13}$C MRS—with CoA-esters a minor metabolic product.[15] Based on these data, but without wishing to be bound by any particular theory, the present inventors believe that the mechanism of [$^{18}$F]FDMA trapping is likely to occur via CoA and carnitine esters.

Figure 2:
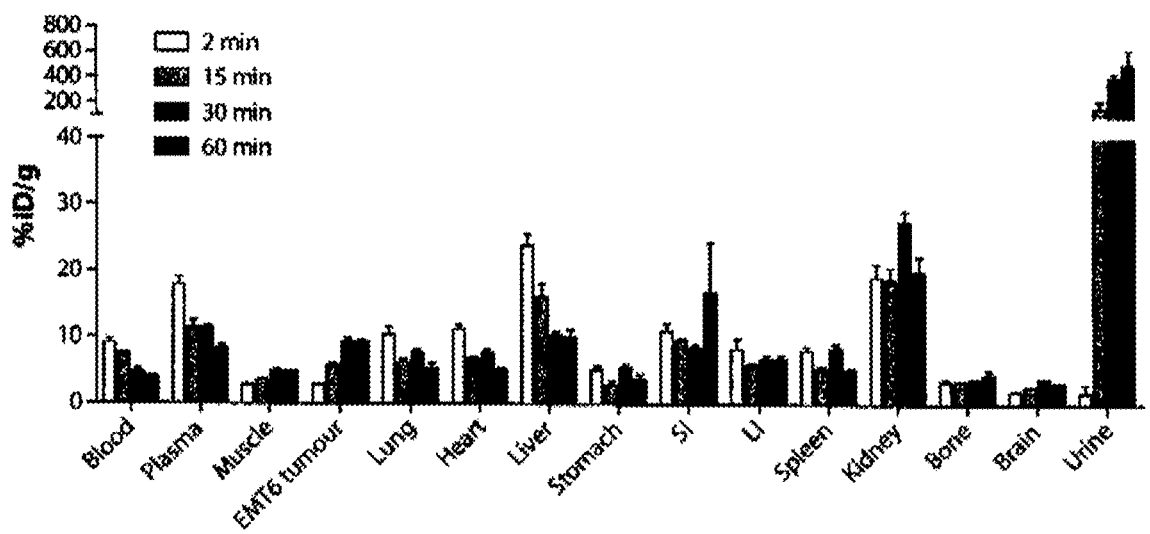
FIG. 2. Biodistribution time course of [$^{18}$F]FDMP in EMT6 xenograft-bearing BALB mice. Approximately 3.7 MBq of [$^{18}$F]FDMP was administered i.v. into anaesthetized animals prior to sacrifice at indicated time points. Tissues were excised, weighed and counted, with counts normalized to injected dose/g wet weight tissue. Mean values (n=3) and SD are shown.
Figure 5:
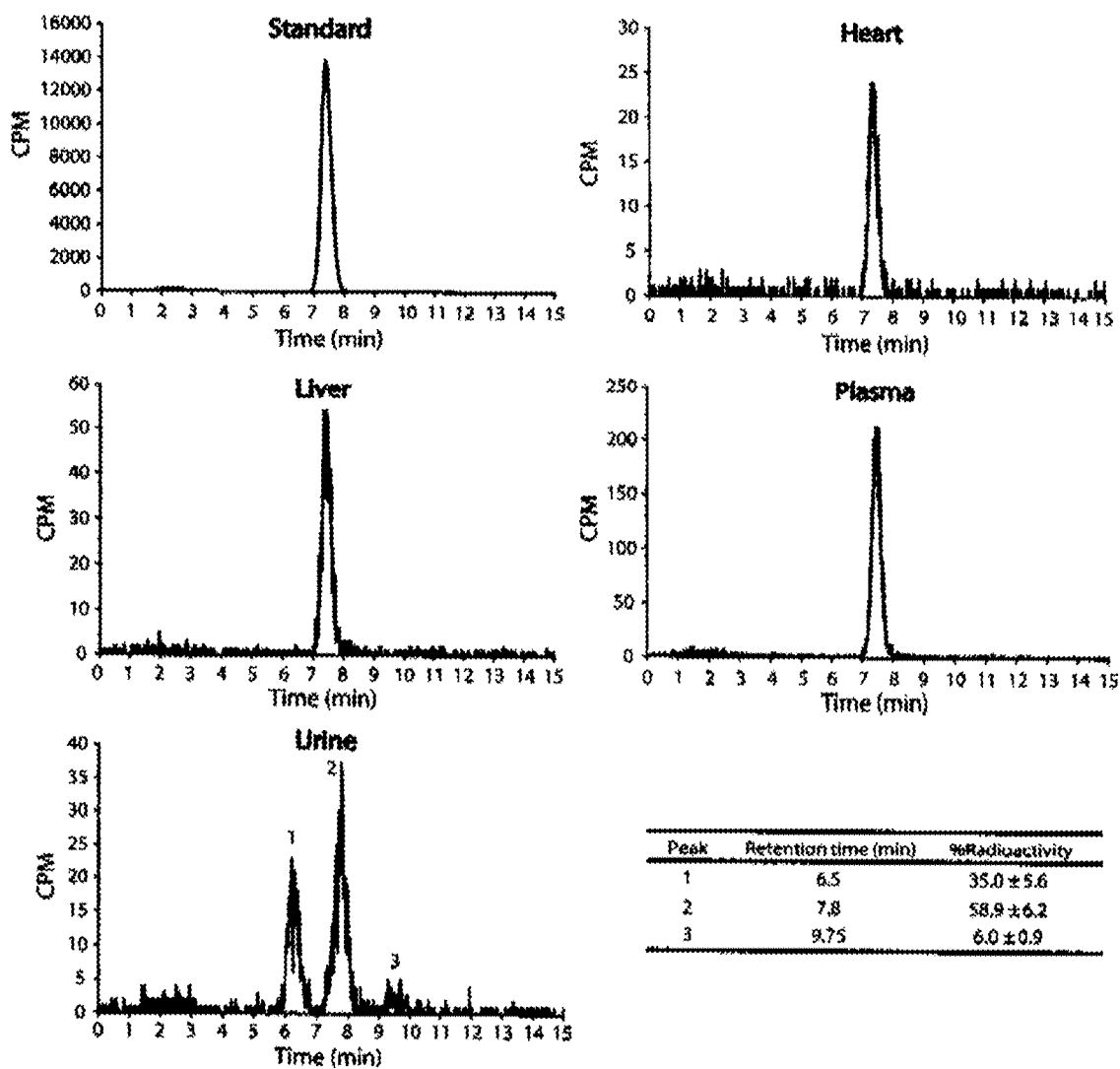
FIG. 5. Representative radio-HPLC analysis of mouse tissue extracts. Tissues were obtained 30 min after i.v. injection of [$^{18}$F]FDMP into non-tumour-bearing BALB/c mice and compared to injection-ready [$^{18}$F]FDMP as a standard. Figure table—urine metabolite analysis. Percentage urine radioactivity of [$^{18}$F]FDMP (peak 2; retention time 7.8 min) and unknown metabolites (peak 1, retention time 6.5 min; and peak 3, retention time 9.75 min) are shown. Mean±SD (n=3 mice).

Time course biodistribution studies revealed organ-specific variations in [$^{18}$F]FDMP retention and pharmacokinetics, characterized by initial uptake in the liver and clearance through the urinary tract (FIG. 2). In agreement with previously published data on carnitine-acylcarnitine distribution,[17] liver-associated [$^{18}$F]FDMP rapidly equilibrated with the plasma compartment. The relatively high plasma half-life of [$^{18}$F]FDMP, observed by the present inventors, is almost certainly accounted for by the high reabsorption rate of small chain fatty acids by the proximal tubules,[18] with FDMP and its metabolites excreted into the urine (FIG. 5). The distribution profile of [$^{18}$F]FDMP in other organs is also in keeping with known tissue pharmacokinetics of pivalic acid in rodents.[19]

Figure 12:
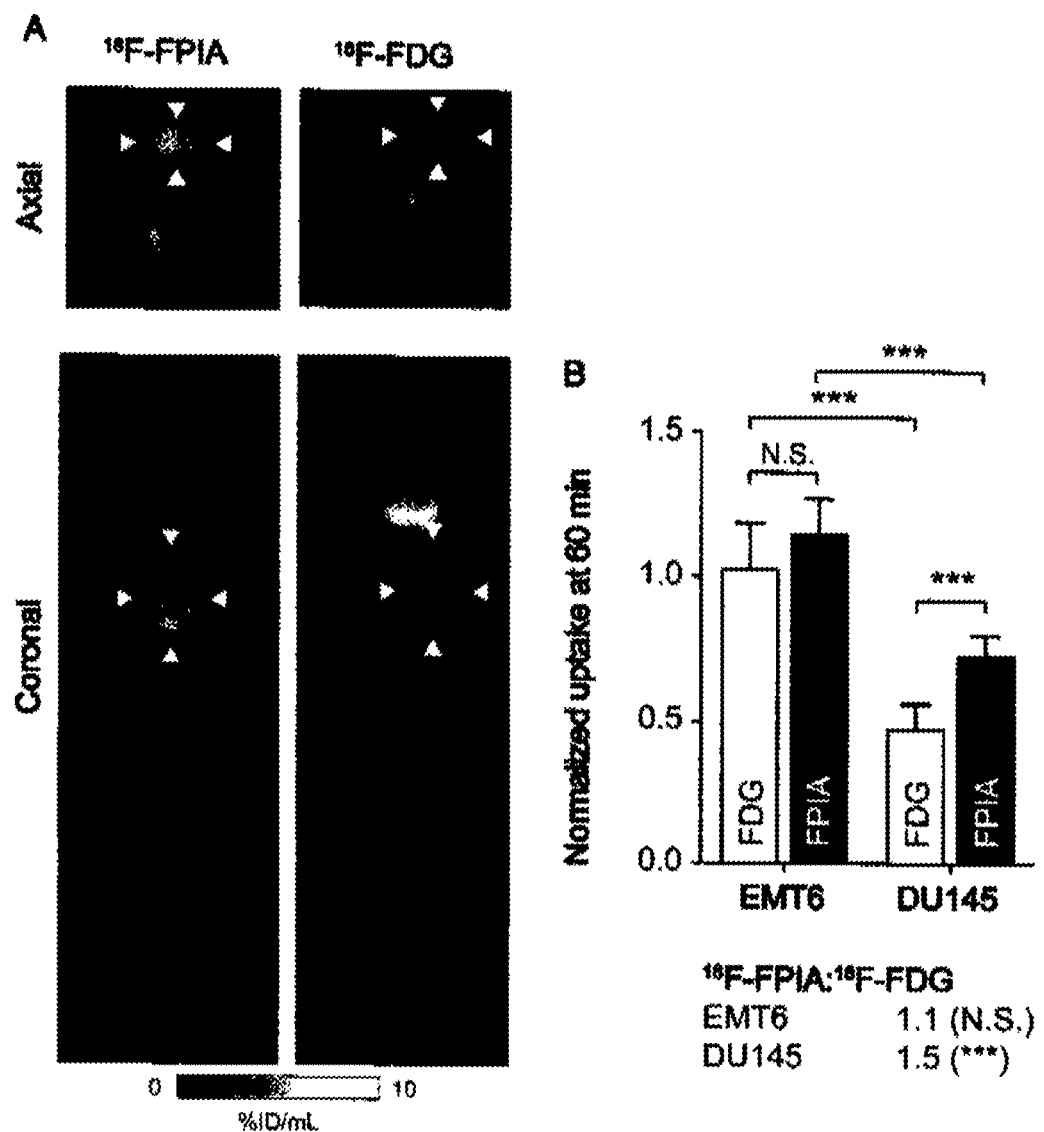
FIG. 12. Prostate tumour imaging with [$^{18}$F]FDMP and [$^{18}$F]FDG-PET. (A) Representative axial and coronal PET images of DU145 tumour-bearing mice (50-60 minutes of summed activity) for [$^{18}$F]FDMP and [$^{18}$F]FDG. (B) Semi-quantitative tumour uptake values for DU145 and EMT6 tumours, extracted from the PET images and normalized to whole-body radioactivity. Mean±SD (n=4 mice per group). *** P<0.001; N.S., not significant.

The present inventors have further showed that [$^{18}$F] FDMP preferentially accumulates in tumours of the breast, brain and prostate. It is thought that upregulation of enzymatic activity (e.g. acetyl CoA synthetase, CRAT), decreased OCTN2 expression or elevated pools of metabolic intermediates may account for increased tumour-to-normal tissue retention. High serum carnitine (~60 μM in healthy adult males[20]) may further enhance [$^{18}$F]FDMP tumour retention; analogous to the increased uptake measured in cell experiments following addition of exogenous carnitine. The present inventors compared tumoural [$^{18}$F]FDMP uptake to [$^{18}$F]FDG uptake and retention. Although it was impossible to differentiate between the two radiotracers by normalized uptake values in breast adenocarcinoma xenografts (FIG. 7), [$^{18}$F]FDMP radiotracer retention was 54% higher in prostate tumours than with [$^{18}$F]FDG, indicating the potential utility for [$^{18}$F]FDMP for prostate cancer detection (FIG. 12).

Figure 8:
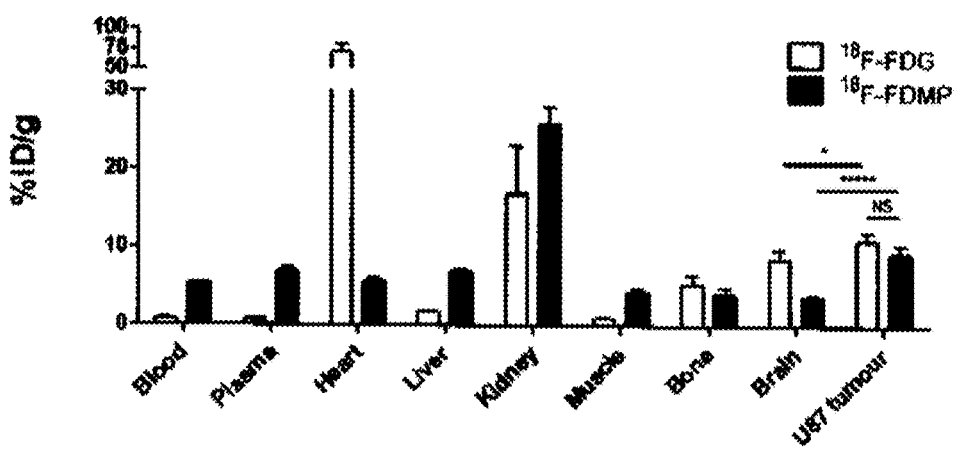
FIG. 8. [$^{18}$F]FDMP and [$^{18}$F]FDG biodistribution in U87 human glioblastoma-bearing BALB/c nude mice. Approximately 3.7 MBq of radiotracer was administered i.v. into anaesthetized animals prior to sacrifice at 60 min post injection. Tissues were excised, weighed and counted, with counts normalized to injected dose/g wet weight tissue. Mean values (n=3) and SD are shown. *, P<0.05; *****, P<0.00005. Abbreviations: NS, not significant.

The present inventors further observed that [$^{18}$F]FDMP uptake was significantly lower than [$^{18}$F]FDG in the normal brain. The improved human glioma tumour:brain ratio of 2.5 for [$^{18}$F]FDMP, versus 1.3 for [$^{18}$F]FDG could be advantageous for [$^{18}$F]FDMP visualization of brain tumours when compared with [$^{18}$F]FDG (FIG. 8). Comparison of [$^{18}$F]FDMP with radiolabeled amino acids [$^{11}$C]MET, [$^{18}$F]FET, and [$^{18}$F]DOPA in an orthotopic setting will provide further insight into the effectiveness of [$^{18}$F]FDMP for imaging tumours of the brain.

The present inventors have noted that [$^{18}$F]FDMP does not appear to provide an advantage over [$^{18}$F]FDG for the differential diagnosis of cancer versus inflammation (FIG. 13)[21]. [$^{18}$F]FDMP and related compounds may therefore have utility as radiotracers in non-malignant inflammation related pathologies including Alzheimer's disease and multiple sclerosis.

Synthesis

As radionuclides have limited half-life, convenient, reliable and rapid syntheses for the provision of compositions according to the present invention are highly desirable. Accordingly, in one aspect the present invention provides methods for the synthesis of radionuclide-labelled carboxylic acids of the invention and precursors thereof.

Suitable syntheses for some compounds of the present invention may begin with the corresponding hydroxyl-substituted ester (the hydroxyl substituent being at the position at which the radionuclide is to be introduced). The ester may be an optionally substituted alkyl ester or an optionally substituted phenyl or benzyl ester. The radionuclide may be introduced into this precursor through nucleophilic substitution, preferably through an $S_N2$-type mechanism. Consequently, the hydroxyl substituent to be displaced is converted to a suitable leaving group, for example, by mesylation or tosylation using methods known in the art.

For example, tosylation may be used to convert a beta-hydroxyl substituent into a suitable leaving group as detailed below,

wherein $R^1$, $R^2$ and $R^3$ are independently $C_{1-4}$alkyl, preferably methyl. This leaving group may then be displaced by a suitable radionuclide nucleophile to generate an ester of a radiolabelled nuclide of the invention. The following scheme shows the reaction for [$^{18}$F]fluorine. This example is provided by way of illustration and not by way of limitation, and any suitable Finkelstein-type reaction may be used to introduce a appropriate radionuclide label comprising, for example [$^{76}$Br]bromine, [$^{123}$I]iodine, [$^{124}$I]iodine, or [$^{125}$I] iodine.

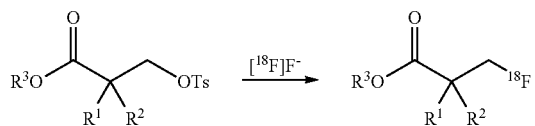

Suitable [$^{18}$F]fluoride nucleophiles include, but are not limited to, kryptand complexes of [$^{18}$F]F$^-$ formed in the presence of a base. A preferred kryptand is Kryptofix® $K_{222}$. Suitable bases include potassium carbonate and potassium hydrogen carbonate. In some embodiments, potassium hydrogen carbonate may be preferable as a less basic environment may disfavour hydrolysis of some ester groups. A further suitable [$^{18}$F]fluoride nucleophile is [$^{18}$F]TBAF, which may be obtained by combining the generated [$^{18}$F] fluoride with a suitable tetrabutylammonium salt, preferably tetrabutyl-ammonium hydrogen carbonate. Analogous to the details provided above, the use of tetrabutylammonium hydrogen carbonate rather than other tetrabutylammonium salts may be preferably in certain embodiments owing to a reduced tendency to undesired ester hydrolysis attributed to the basicity of the solution. In some methods according to the present invention, the step of nucleophilic displacement with a [$^{18}$F]fluoride nucleophile is performed at a temperature between 90° C. and 120° C., preferably about 105° C. and/or lasts for between 5 and 15 minutes, preferably about 10 minutes. The resultant product may be purified using reverse-phase preparative HPLC (30% ethanol/water) and/or using solid phase extraction using, for example, a C18 cartridge.

Suitable reagents for the inclusion of other radionuclide labels, for example, [$^{11}$C]carbon, [$^{13}$N]nitrogen, [$^{15}$O]oxygen, or other isotopes such as [$^{13}$C]carbon may include appropriately labelled organocuprate Grignard-type reagents, amines, and alcohols. For example, to introduce a [$C^L$]carbon label a substitution reaction using a suitable dialkylcuprate of general formula $R^*_2CuLi$, wherein $R^*$ is [$C^L$]carbon-labelled alkyl group, for example, [$^{11}$C] or [$^{13}$C] methyl, may be used. [$C^L$]carbon may refer to the naturally most abundant carbon isotope, [$^{12}$C]carbon or to either a [$^{11}$C] or [$^{13}$C]carbon as appropriate. As detailed above, the resultant product may be purified using preparative HPLC and/or using solid phase extraction using, for example, a C18 cartridge, as appropriate.

An alternative approach to the introduction of a radionuclide carbon or carbon isotope suitable for imaging using MRS or MRI following hyperpolarisation by DNP into some compounds of the invention may begin with a suitable acrylate. Use of a dialkylcuprate typically favours the desired 1,4-addition in preference to 1,2-addition.

To obtain the corresponding labelled carboxylic acids of the invention, the ester moiety is hydrolysed. Hydrolysis may be performed under basic conditions, for example using an aqueous solution of a suitable alkali or alkali earth hydroxide such as sodium hydroxide. In some methods of the present invention, the hydrolysis step is performed at a temperature between 50° C. and 70° C., preferably at 60° C. and/or lasts for less than 10 minutes, preferably 5 mins.

To prepare suitable compositions, methods of the invention may further comprise the step of neutralising the resultant labelled carboxylic acid with an acid, for example, hydrochloric acid, and a suitable buffer, for example, a phosphate buffered saline solution, to achieve a composition of pH suitable for administration. In some methods of the present invention, the pH is adjusted to between pH 7 and pH 8, preferably between pH 7.2 and pH 7.6, more preferably to about pH 7.4. Some compositions obtained by methods of the invention have 10% EtOH/PBS or less. Alternatively, in some methods according to the present invention, ethanol may be removed after neutralisation at 40-50° C. under vacuum to give a composition substantially free of ethanol.

Preferably the resulting composition is suitable for injection into a subject without the need for further purification, treatment or processing. However, should further purification be required or desirable, the resulting composition may be purified using solid phase extraction techniques, for example, using an ion exchange cartridge. In preferred embodiments of the present invention in which the label is an [$^{18}$F]fluorine and the provision of said composition suitable for injection into a subject is achieved in less than 120 min from when the aqueous fluoride is delivered and the drying step begins.

As detailed above, it may be desirable to incorporate a carbon isotope, for example, [$^{11}$C] or [$^{13}$C]carbon, and this may be incorporated at the 1-position, that is, at the carboxy carbon. A suitable method for this incorporation may utilise a Grignard reaction followed by quenching of the corresponding anion derived from the bromo-precursor as detailed below:

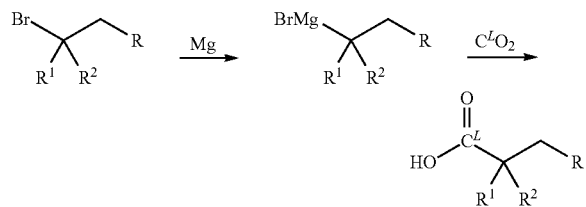

$C^LO_2$ is [$^{13}$C]CO$_2$ or [$^{13}$C]CO$_2$ as appropriate, and R is selected from H, F, $C_{1-4}$alkyl and OH, wherein the OH may be protected with a suitable protecting group.

If R is OH or a protected form thereof, the above method may be useful for the generation of tosylate precursors suitable for use in the synthesis detailed above. Alternatively, the above sequence may be performed when R is fluorine or a suitable radionuclide, for example [$^{18}$F]fluorine. Preferred compounds of the invention which may be obtainable using this method include optionally substituted [1-$^{11}$C]-2,2-$C_{1-4}$-dialkylpropanoic acids and [1-$^{13}$C]-2,2-$C_{1-4}$-dialkyl propanoic acids, for example, [1-$^{11}$C]FDMP, [1-$^{13}$C]FDMP, and [$^{18}$F][1-$^{13}$C]FDMP.

The invention will now be further described with reference to the following examples. These are provided as a means of illustration and are not intended to limit the invention.

EXAMPLES

Experimental Procedures

Synthesis of [$^{18}$F]FDMP

Methyl 2,2-dimethyl-3-(p-tolylsulfonyloxy)propanoate precursor

Methyl 3-hydroxy-2,2-dimethylpropanoate (193 μL, 1.5 mmol) was dissolved in dry pyridine (0.5 mL) and DMAP (9.2 mg, 0.075 mmol) in pyridine (0.5 mL) was added. Tosyl chloride (347 mg, 1.8 mmol) in pyridine (2 mL) was then added and the reaction mixture was stirred at room temperature under nitrogen atmosphere for 3 h. The reaction was diluted with CH$_2$Cl$_2$ (30 mL) and water (50 mL). Phases were separated and aqueous layer was extracted with CH$_2$Cl$_2$ (2×30 mL). Combined organic layers were washed with 1 M HCl (2×50 mL) and brine (50 mL) and dried over Na$_2$SO$_4$. The salt was then filtered off, the reaction mixture concentrated in vacuo and the residue purified by chromatography on silica gel (15% EtOAc/PE). The title compound was isolated as a white solid (270 mg, 70% yield) $^1$H NMR (400 MHz, CDCl$_3$) δ 7.81 (d, J=8.3 Hz, 2H; Ar), 7.37 (d, J=8.0 Hz, 2H; Ar), 4.03 (s, 2H; 3-H), 3.63 (s, 3H; OMe), 2.48 (s, 3H; Ph-Me), 1.21 (s, 6H; CH$_3$-2); $^{13}$C NMR (101 MHz, CDCl$_3$) δ 175.1 (s; CO), 144.9 (s; Ar), 132.7 (s; Ar), 129.8 (d, 2C; Ar), 128.0 (d, 2C; Ar), 75.1 (t; C-3), 52.2 (q; OCH$_3$), 42.8 (s; CMe$_2$), 22.0 (q, 2C; CMe$_2$), 21.7 (q; Ar-Me); MS[ESI,(%)]: 207 (8, [MH$^+$]), 209 (20, [MNa$^+$]).

[$^{18}$F]-3-fluoro-2,2-dimethyl-propanoic acid

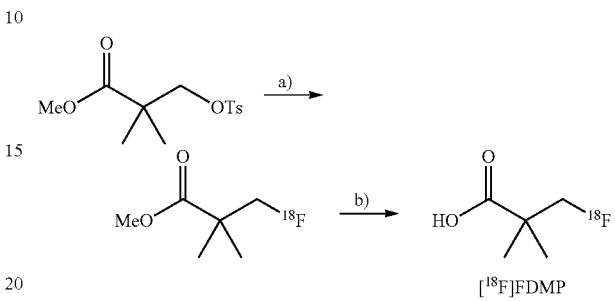

Reagent and conditions: a) K$_2$CO$_3$, K$_{222}$, [$^{18}$F]F$^-$ or KHCO$_3$, K$_{222}$, [$^{18}$F]F$^-$ or [$^{18}$F]TBAF, 105° C. or 120° C., 10 min. b) NaOH (1M), 60° C., 5 min then HCl (1M) and PBS, or NaOH (1M), 60° C., 5 min then HCl (1M) and 45° C. in vacuo and PBS/ a. The methyl 2,2-dimethyl-3-(p-tolylsulfonyloxy)propanoate precursor was then taken forward for radiochemistry. Initial experiments to incorporate fluorine-18 were carried out using K$_2$CO$_3$ and kryptofix to form the K$^{18}$F/kryptand complex, followed by addition of the precursor in acetonitrile at 80° C. The reaction was monitored by analytical HPLC. These conditions gave a mixture of radiolabelled products after 5 minutes and only 6% product; further heating led to decomposition of the precursor and only 12% product. The reaction was then undertaken using DMF as solvent at 105° C., and this showed a robust reaction, giving the product (up to 75% of radiolabel incorporation) and [$^{18}$F]toluenesulfonyl fluoride (25% yield) as a by-product after 15 minutes. At this temperature the precursor was degraded to give methyl 3-hydroxy-2,2-dimethylpropionate. The intermediate was then isolated using reverse phase preparative HPLC and 30% ethanol/water as the eluent. The yield of the isolated compound was lower than expected from the ratio of conversion. It was suspected that on dilution of the reaction mixture with water, hydrolysis of the methyl ester had occurred giving the final desired product [$^{18}$F]FDMP. The product could not be isolated as it co-eluted at the solvent front with the DMF and any unreacted fluoride-18. Due to hydrolysis, the isolated yield of the methyl ester intermediate was lower than anticipated (13.9±9.1% decay corrected, n=7). As a less basic environment should disfavour the hydrolysis of the methyl ester, KHCO$_3$ was employed instead of K$_2$CO$_3$ to form the kryptand complex. The optimal reaction conditions were found to be heating at 110° C. for 10 min. No other radiochemical peaks apart from the desired product was observed. This gave up to 80% of incorporation of the fluoride as shown by analytical HPLC (40% MeOH/water) and improved the yield of the isolated product to 29.6±19.6% decay corrected (n=6).

Good results were also obtained when [$^{18}$F]TBAF was used as source of fluoride. The fluoride was dried in the presence of tetrabutylammonium hydrogen carbonate (TBAHCO$_3$) to give [$^{18}$F]TBAF. The use of the less basic TBAHCO$_3$ led to reduced hydrolysis before preparative HPLC. Analysis of the reaction mixture showed complete incorporation of fluoride to give the desired product. After addition of water to the reaction mixture, the preparative HPLC showed 44% intermediate product and 52% of the hydrolysed final product, together with unreacted fluorine-18. The methyl ester protected intermediate was isolated in 37% decay corrected yield.

b. Once isolated from the HPLC eluent, the intermediate product was hydrolysed using NaOH (1M) in 5 min at 60° C. which was then neutralised with HCl and phosphate buffered saline added to achieve a pH of 7.4 and 10% EtOH/PBS or less.

Alternatively, and preferably, after neutralization with HCl, EtOH was removed under vacuum at 45° C. and the final solution was buffered with PBS.

In total, the entire synthesis and formulation of [$^{18}$F]FDMP from the methyl 2,2-dimethyl-3-(p-tolylsulfonyloxy)propanoate precursor takes 1.5 h and delivers [$^{18}$F]FDMP ready for injection in EOS of 11.3±4.1% (n=4).

One of the following methods may be used to prepare a dose of a composition according to the present invention that is suitable for administration:

Method A. Aqueous [$^{18}$F]fluoride was trapped into a QMA cartridge and eluted into a 2 mL Wheaton vial with K$_2$CO$_3$ (200 µL of a 12 mg/mL stock solution) and K222 (800 µL of a 18 mg/L stock solution). The fluoride was dried at 120° C. and an azeotrope of MeCN (1 mL) used to aid drying. Methyl 3-tolylsufonyloxy-2,2-dimethyl-propanoate (8 mg) in DMF (300 µL) was added and the reaction mixture was heated at 105° C. for 10 min and then cooled down to 30° C. using compressed air. The reaction mixture was quenched with water (700 µL) as labelled intermediate methyl [$^{18}$F]-3-fluoro-2,2-dimethyl-propanoate isolated by semipreparative HPLC [Gemini C18 (100×10 mm) column, isocratic 30% EtOH/water method, rt=9 min]. NaOH (1M, 200 µL) was added and the mixture heated at 60° C. for 5 min, cooled down to room temperature and neutralized with HCl (1M) and PBS to reach neutral pH. Ethanol was removed under vacuum at 45° C., the solution buffered with PBS and injected without further treatment.

Method B. KHCO$_3$ (200 µL of a 12 mg/mL stock solution) was used instead of K$_2$CO$_3$ and the labelling carried out as previously described.

Method C. Aqueous [$^{18}$F]fluoride was dried in the presence of TBAHCO$_3$(1.5 M, 22 µL) and the labelling carried out as previously described.

Method D. The radiosynthesis of [$^{18}$F]FDMP was automatically performed on a Siemens Explora RN+LC platform. Aqueous [$^{18}$F]-fluoride was trapped into a QMA cartridge preconditioned with water (1 mL) and eluted into a 5 mL Wheaton vial with KHCO$_3$ (100 µL of a 12 mg/mL stock solution in water) and K222 (400 µL of a 18 mg/mL stock solution in water). The fluoride was dried at 105° C. and an azeotrope of MeCN (0.5 mL×2) used to aid drying. Precursor 1 (8 mg) in DMF (450 µL) was added and the reaction mixture was heated at 120° C. for 10 min and then cooled down to 30° C. The reaction mixture was quenched with water (4 mL) and labeled intermediate [$^{18}$F]2 isolated by semipreparative column, isocratic 20% EtOH/water method, flow rate 5 mL/min, retention time (rt)=10 min]. NaOH (1 M, 200 µL) was added and the mixture heated at 60° C. for 5 min then cooled down to 45° C. Ethanol was removed at 45° C. under vacuum for 30 min and the mixture neutralized with HCl (1 M, ~200 µL).

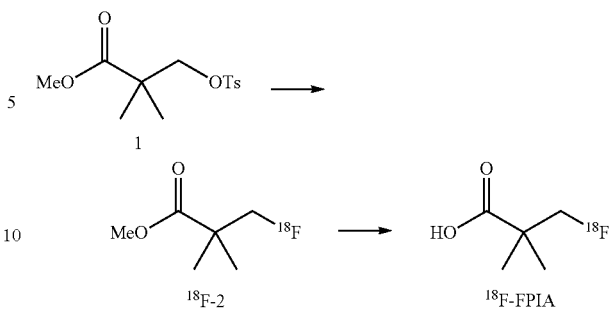

As explained elsewhere, the terms FPIA and FDMP are alternate names for the same compound.

[$^{18}$F]FDMP In Vivo Testing in Mice by PET Imaging

[$^{18}$F]FDMP was used in initial experiments by the inventors in healthy mice and showed good distribution within the animals and no defluorination of the tracer, otherwise leading to non-specific retention in bones (PET/CT, FIG. 1). Substantial uptake of [$^{18}$F]FDMP was observed in the cortex of the kidney, with clearance primarily via urinary excretion. Tracer localisation was also observed in the heart, liver and intestines.

Figure 3:
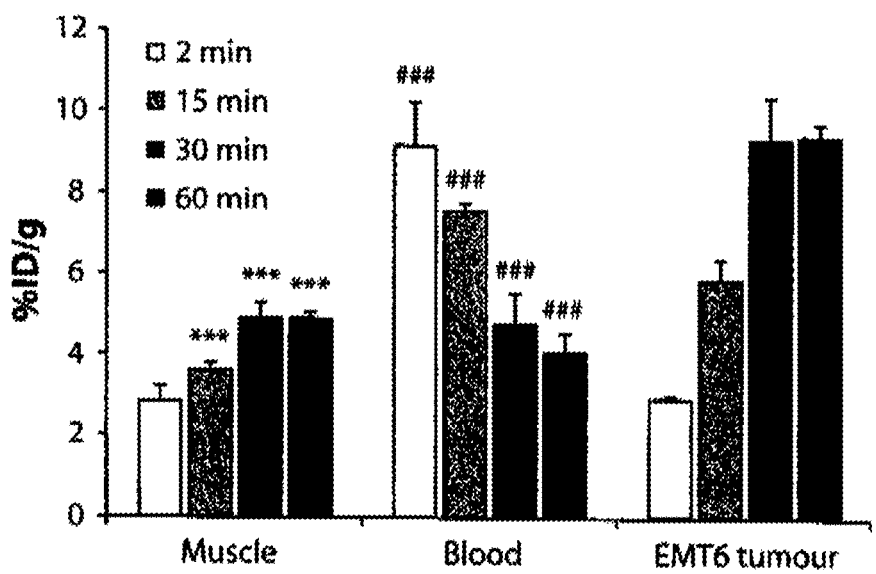
FIG. 3. Comparison between EMT6 tumour xenograft and background tissue [$^{18}$F]FDMP radioactivity. Values were obtained from time course biodistribution studies. Mean values and SD are shown (n=3). ***, P<0.005 tumour/muscle ratio; ###, P<0.005 tumour/blood ratio.

FIG. 2 shows the biodistribution of [$^{18}$F]FDMP in EMT6 murine breast adenocarcinoma xenografts 2, 15, 30 and 60 minutes after administration as a function of % ID/g (percentage injected dose per gram tissue). Of particular note is the low bone uptake which is indicative of minimal defluorination. FIG. 3 shows the tumour (EMT6) to tissue ratio of [$^{18}$F]FDMP 2, 15, 30 and 60 minutes after administration. The data show good target:background ratio.

Figure 6:
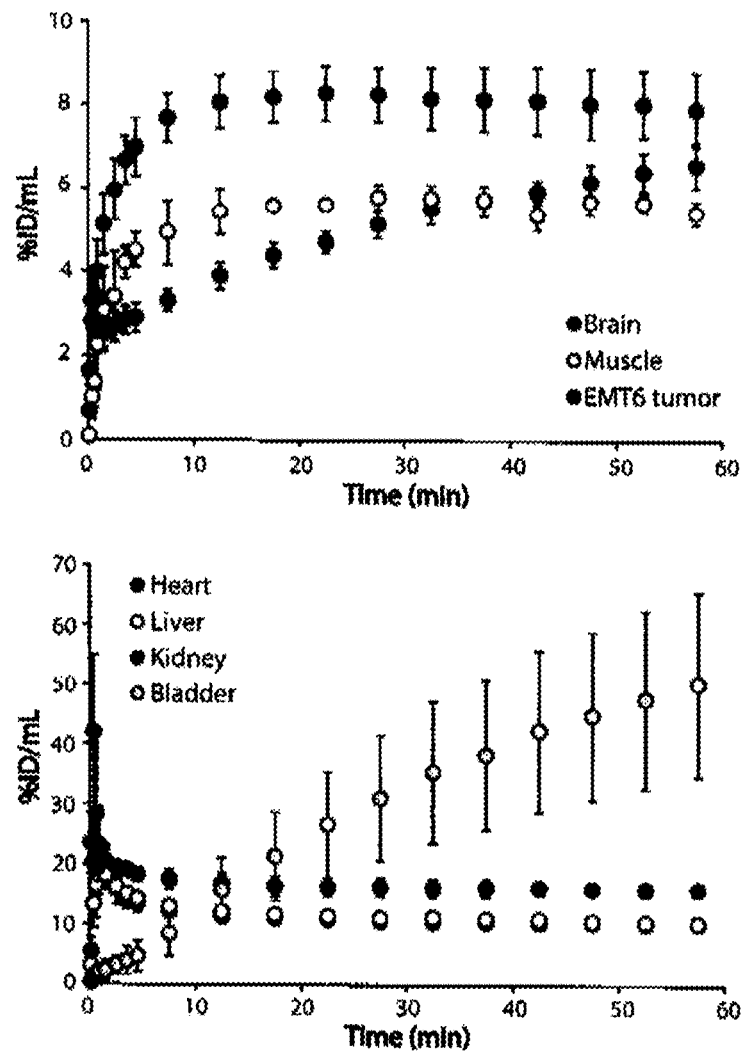
FIG. 6. Time course of [$^{18}$F]FDMP uptake in vivo in EMT6 murine breast adenocarcinoma xenografts in comparison to normal healthy tissues. Mean values and SD are shown (n=3). 30 to 60 min cumulative images of the dynamic data were employed to define 3-dimensional (3D) regions of interest (ROIs). The count densities were averaged for all ROIs at each time point to obtain a time versus radioactivity curve (TAC), normalised for injected dose.
Figure 7:
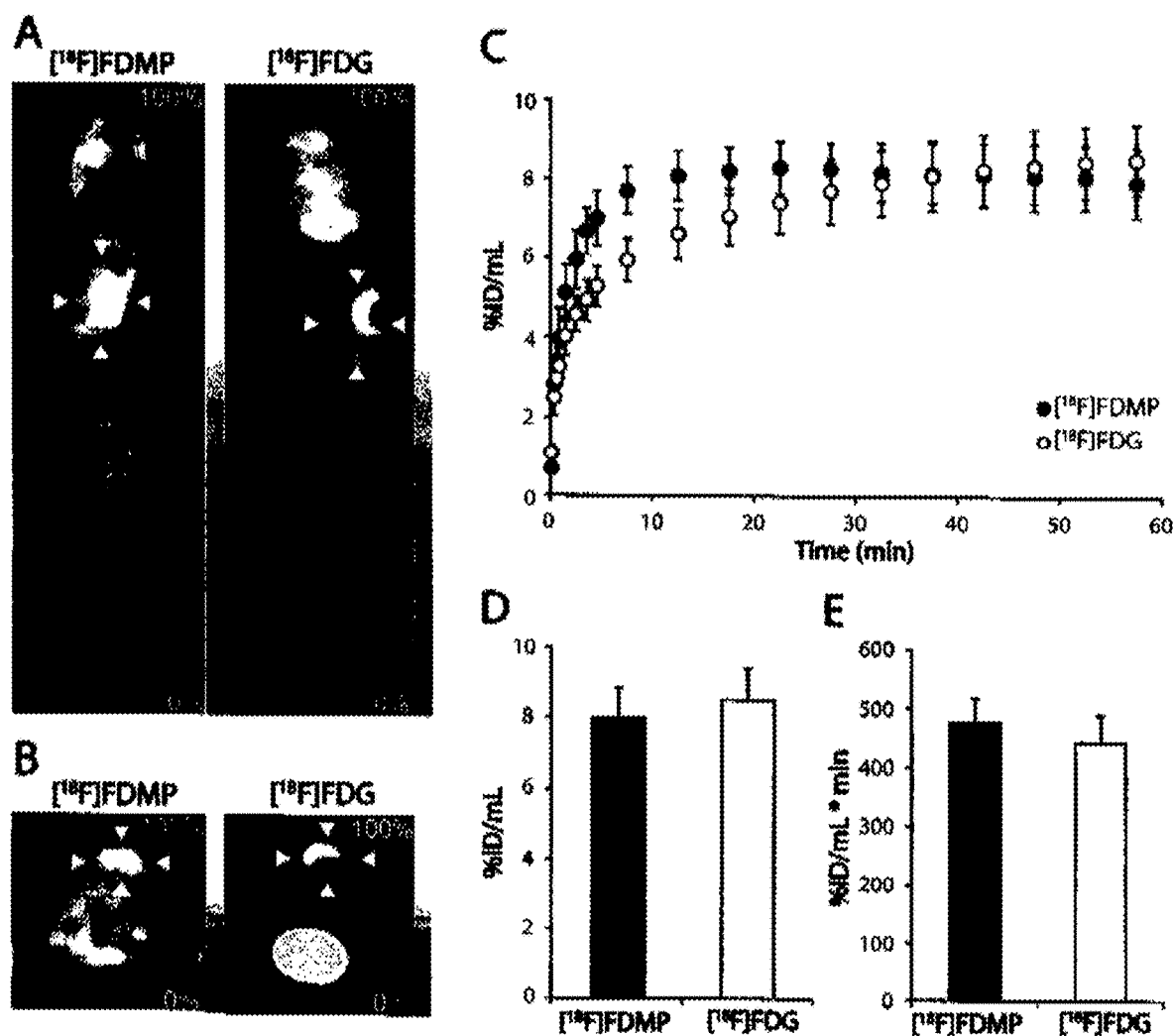
FIG. 7. Dynamic [$^{18}$F]FDG- and [$^{18}$F]FDMP-PET image analysis. (A) Representative coronal PET-CT images (30-60 minutes of summed activity) for [$^{18}$F]FDMP and [$^{18}$F]FDG. (B) Representative axial PET-CT images of EMT6 tumour-bearing mice (30-60 minutes of summed activity) for [$^{18}$F]FDMP and [$^{18}$F]FDG. White arrowheads indicate the tumour, identified from the CT image. (C) EMT6 tumour time versus radioactivity curve (TAC) obtained from 60-minute dynamic PET imaging. Mean±SD (n=5 mice per group). (D & E) Semi-quantitative imaging variables extracted from the TAC. (D) Average tumour-associated counts at 60 min, normalised for injected dose. (E) Area under the tumour TAC. Mean±SD (n=4 mice per group).

Another advantage of [$^{18}$F]FDMP is its desirable uptake time (FIG. 4) and stability, in particular, its inability to be a substrate for cellular metabolism. HPLC chromatograms of analytes extracted from tissues 30 min post [$^{18}$F]FDMP injection showed no degradation of FDMP within the body, besides in urine (FIG. 5). [$^{18}$F]FDMP is able to cross the blood-brain barrier (FIG. 6) and, owing to its low background levels, may have utility as an imagining agent for brain tumour detection. [$^{18}$F]FDMP compares favourably to [$^{18}$F]FDG in vivo. FIG. 7 shows comparable tumour uptake and retention of [$^{18}$F]FDMP and [$^{18}$F]FDG, confirmed by semi-quantitative parameters derived from the TAC: normalized uptake values at 60 min and values for the tumour area under the time versus radioactivity curve, while FIG. 8 shows that [$^{18}$F]FDMP provides a superior target:background ratio compared to [$^{18}$F]FDG in U87 glioma human xenografts.

Cell Culture

EMT6 murine breast cancer cells (LGC Standards) were grown in Waymouth's medium (Life Technologies), with U87 human glioma cells (LGC Standards) grown in DMEM medium (Life Technologies). DU145 (kind donation from Dr. Almut Schulze, CRUK London Research Institute) and BT474 (LGC Standards) were grown in RPMI (Life Technologies). All media were supplemented with 2.5 mL penicillin/streptomycin (10,000 IU·mL$^{-1}$/10,000 mg.mL$^{-1}$) and 2 mM L-glutamine (Life Technologies). Waymouth's medium contained 15% fetal calf serum (FCS), with 10% FCS added to DWEM and RPMI. All cells were propagated at 37° C. in a humidified atmosphere containing 5% CO$_2$.

Materials

[$^{18}$F]FDMP was obtained in end of synthesis yield (EOS) of 7.68±4.99 (n=9) in approximately 90 min from aqueous fluoride to formulation. [$^{18}$F]FDG was purchased from PETNET solutions (Siemens).

[$^{18}$F]FDMP Uptake in Cells

EMT6 cells (2×10$^5$) were plated into 6-well plates overnight prior to analysis. On the day of the experiment fresh growth medium containing 0.74 MBq [$^{18}$F]FDMP were added to individual wells (1 mL/well). Cell uptake was measured over 60 min post radiotracer addition. Plates were placed on ice, washed 3 times with ice-cold PBS and lysed in RIPA buffer (Thermo Fisher Scientific Inc.; 1 mL, 10 min). Cell lysates were transferred to counting tubes and decay-corrected radioactivity was determined on a gamma counter (Cobra II Auto-Gamma counter, Packard Biosciences Co.). Aliquots were snap-frozen and used for protein determination following radioactive decay using a BCA 96-well plate assay (Thermo Fisher Scientific Inc.). In addition, 10 μL standards from a 0.74 MBq/mL stock solution were counted to quantitate % radiotracer uptake. For carnitine treatment, cells were incubated with 10 μM L-carnitine for the duration of the uptake time course.

Metabolism Experiments in Cells

BT474 cells were seeded in 12-well plates at 2×10$^5$ cells per well. For measurement of FDMP uptake, the media was replaced with media supplemented with 500 μM FDMP and incubated for the indicated times. All media samples were harvested at the same time and immediately diluted into ice-cold extraction solution of methanol, acetonitrile, and water (5:3:2) (All chemicals were purchased from Fisher Scientific and were LC-MS grade). Cell numbers were assumed to be identical. The amount of extraction solution added to each well was determined by cell counts obtained from a counting plate run in parallel (1 mL/2×10$^6$ cells). Extracts were vortexed for 10 min at 4° C. and then centrifuged at 16,500 g at 4° C. for 15 min. Supernatants were removed and analyzed by LC-MS (ZIC-pHelic HPLC columns and Exactive Plus Orbitrap MS (ThermoScientific). Data was analyzed using Xcalibur and LCQuan software (ThermoScientific). FDMP and FAC standards were run in isolation for quantification.

In Vivo Tumour Models

All animal experiments were performed by licensed investigators in accordance with the United Kingdom Home Office Guidance on the Operation of the Animal (Scientific Procedures) Act 1986 and within the published guidelines for the welfare and use of animals in cancer research.[22] EMT6 tumour cells (2×10$^6$; 100 μL PBS) were injected subcutaneously on the back of female BALB/c mice (aged 6-8 weeks; Charles River) and grown to ~150 mm$^3$. U87 tumours were grown following subcutaneous injection of 5×10$^6$ cells (100 μL PBS) on the back of female BALB/c nude mice (aged 6-8 weeks; Charles River), with BT474 tumours induced following injection of 5×10$^6$ cells in matrigel (BD Biosciences; 1:1 ratio PBS-to-matrigel; 100 μL total). Tumour dimensions were measured periodically using a caliper and tumour volumes were calculated by the equation: volume=(n/6)×a×b×c, where a, b, and c represent three orthogonal axes of the tumour. Inflammation was performed in an aseptic inflammation model as previously described.[23]

In Vivo Radiotracer Stability and Metabolism

Radiolabeled metabolites from plasma and tissues were quantified using an adapted method.[24] BALB/c non-tumour-bearing mice under general anesthesia (2.5% isofluorane; non-recovery anesthesia) were administered a bolus i.v. injection of [$^{18}$F]FDMP (~7.4 MBq), and sacrificed by exsanguination via cardiac puncture 30 min post radiotracer injection. Heart, urine and liver samples were immediately snap-frozen in liquid nitrogen. Aliquots of heparinized blood were rapidly centrifuged (14000 g, 5 min, 4° C.) to obtain plasma. Plasma samples were subsequently snap-frozen in liquid nitrogen and kept on dry ice prior to analysis. For analysis, samples were thawed and kept at 4° C. immediately before use. To ice cold plasma and urine (200 μL) was added ice-cold methanol (600 μL) and the resulting suspension centrifuged (14000 g; 4° C.; 3 min). 300 μL of the resulting supernatant was added to 1 mL ice cold mobile phase. Samples were filtered through a hydrophilic syringe filter (0.2 μm filter; Millex PTFE filter, Millipore, Mass., USA) and the sample (~1 mL) then injected via a 1 mL sample loop onto the HPLC for analysis. Tissues were homogenized in ice-cold methanol (1.5 mL) using an Ultra-Turrax T-25 homogenizer (IKA Werke GmbH and Co. KG, Staufen, Germany) and subsequently treated as per plasma and urine samples. Samples were analyzed on an Agilent 1100 series HPLC system (Agilent Technologies, Santa Clara, Calif., USA), using an isocratic method of 10% MeOH in an ion pair buffer prepared as follows and a μBondapak C18 semi preparative HPLC column (Waters, Milford, Mass., USA; 7.8×3000 mm). Ion pair buffer: 1 mM tetrabutylammonium hydroxide (0.799 g/L) adjusted to pH 7.5 with potassium hydrogen phthalate (0.2 g/L) and sonicated for 30 min. Mobile phase was delivered at a flow rate of 3 mL/min.

Biodistribution Studies

[$^{18}$F]FDMP (~3.7 MBq) was injected via the tail vein of anaesthetized EMT6 tumour-bearing BALB/c mice. The mice were maintained under anesthesia and sacrificed by exsanguination via cardiac puncture at 2, 15, 30, 60, 120 or 180 min post radiotracer injection and tissues harvested. Biodistribution studies with BT474 and U87 tumour-bearing nude mice were performed 60 min post [$^{18}$F]FDMP injection. Tissue radioactivity was determined on a gamma counter (Cobra II Auto-Gamma counter, Packard Biosciences Co.) and decay corrected. 10 μL standards from a 1:100 dilution of the stock activity were also counted for data normalization. Plasma was obtained from terminal blood samples following centrifugation (14000 g, 5 min). Data were expressed as percent injected dose per gram of tissue (% ID/g).

PET Imaging Studies

[$^{18}$F]FDMP imaging scans were carried out on a GENISYS[4] small animal PET scanner (Sofie Biosciences), following a bolus i.v. injection of ~1.85 MBq of the radiotracer into tumour-bearing mice. Static scans were acquired for 10 min and images were reconstructed using maximum-likelihood expectation maximization. In a different cohort of mice, dynamic PET imaging was performed on a Siemens Inveon PET module, (Siemens Medical Solutions USA) as described in supplementary materials. Dynamic PET imaging was performed for the [$^{18}$F]FDMP and [$^{18}$F]FDG comparison study in EMT6 tumour-bearing mice. Static scans on the GENISYS[4] were used for all other experiments. Siemens Inveon Research Workplace software was used for visualization of radiotracer uptake in the tumour and to define the three-dimensional volumes of interest (VOI). Tumour radioactivity were normalized to that of the whole body to obtain the normalized uptake value (NUV) to permit comparison of data obtained using the two scanners.

Dynamic [$^{18}$F]FDMP imaging scans were carried out a dedicated small animal PET scanner (Siemens Inveon PET module, Siemens Medical Solutions USA, Inc., Malvern, Pa., USA) following a bolus i.v. injection of ~3.7 MBq of the radiotracer into tumour-bearing mice. Dynamic scans were acquired in list mode format over 60 min. The acquired data were then sorted into 0.5 mm sinogram bins and 19 time frames for image reconstruction (4×15 s, 4×60 s, and 11×300 s), which was done by iterative reconstruction (2D-OSEM). The Siemens Inveon Research Workplace software was used for visualization of radiotracer uptake in the tumour; 30 to 60 min cumulative images of the dynamic data were employed to define 3-dimensional (3D) volumes of interest (VOIs). The count densities were averaged for all VOIs at each time point to obtain a time versus radioactivity curve (TAC). Tumour TACs were normalized to injected dose, measured by a VDC-304 dose calibrator (Veenstra Instruments, Joure, The Netherlands), and expressed as percentage injected dose per mL tissue. The area under the TAC, calculated as the integral of % ID/mL from 0-60 min, and the normalized uptake of radiotracer at 60 min (% ID/mL$_{60}$) were also used for comparisons.

Tumour Cell Uptake and Metabolism

Figure 9:
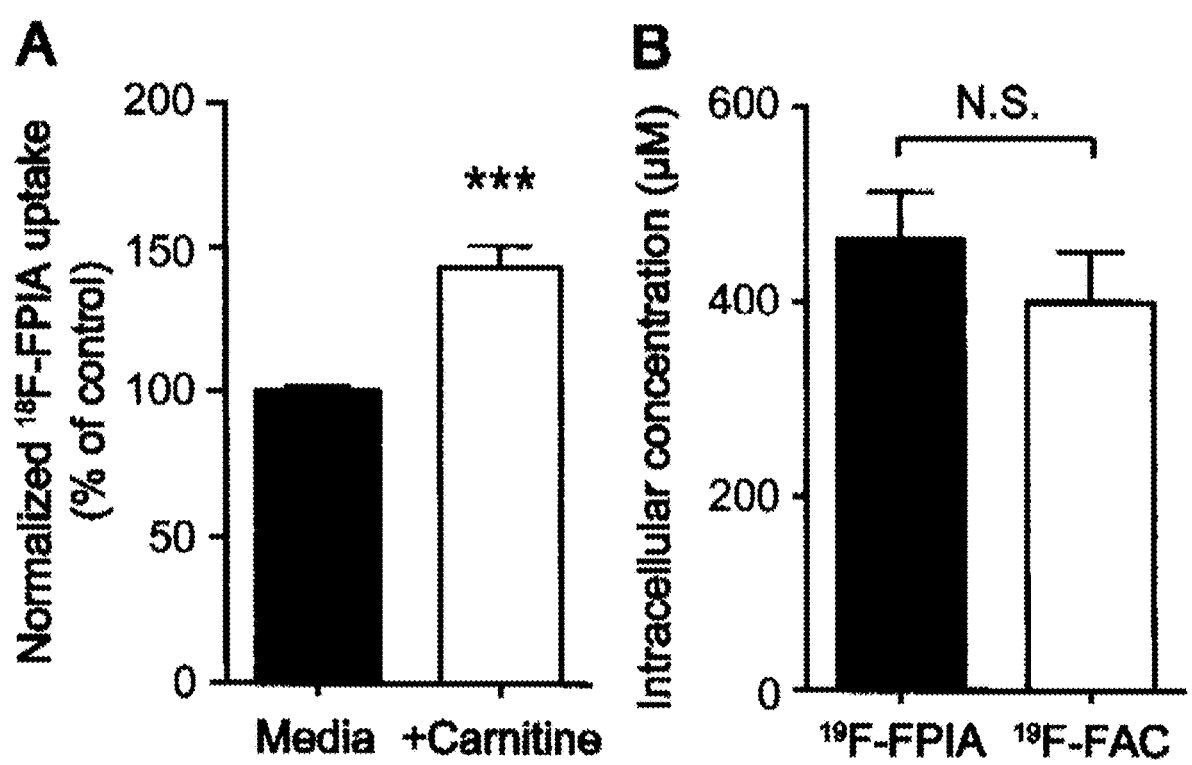
FIG. 9. [$^{18}$F]FDMP uptake and metabolism in cancer cells. (A) Effect of exogenous 10 µM carnitine on [$^{18}$F]FDMP uptake, trapping and retention in EMT6 cells. (B) Intracellular accumulation of [$^{19}$F]FDMP and [$^{19}$F]FAC in human breast adenocarcinoma BT474 cells at 24 h as analyzed by LC-MS. Mean±SD (n=3).
Figure 10:
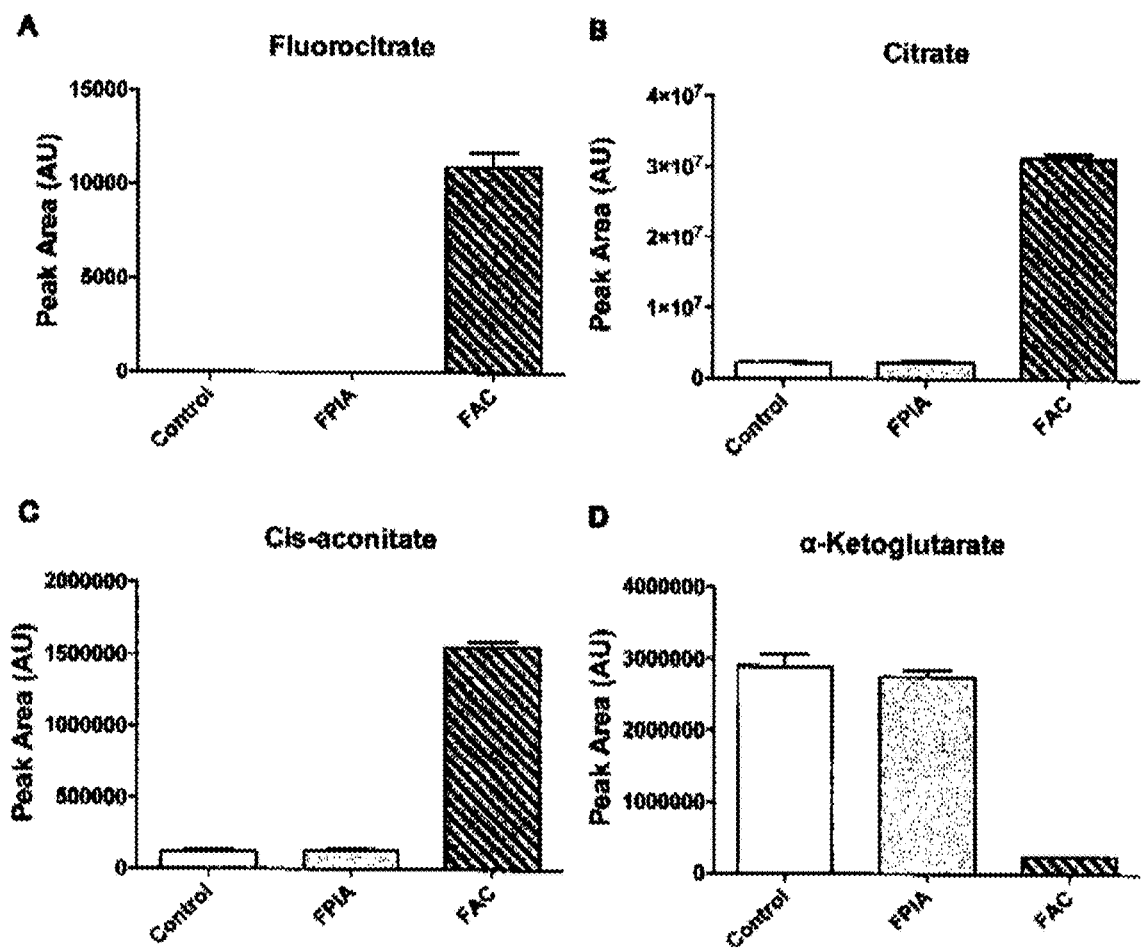
FIG. 10. Effect of exogenous [$^{19}$F]FDMP and [$^{19}$F]FAC on intracellular metabolite concentrations of fluorocitrate (A), citrate (B), cis-aconitate (C) and α-ketoglutarate pools (D) as analyzed by LC-MS. AU, arbitrary units.

Uptake of [$^{18}$F]FDMP into EMT6 tumour cells was linear over the initial 30 min of incubation, reaching 1.40±0.10% radioactivity/mg protein. By 60 min post radiotracer addition, cell uptake had plateaued at 1.47±0.04% radioactivity/mg protein (FIG. 4). [$^{18}$F]FDMP uptake increased by 44% compared to control cells following incubation with 10 μM L-carnitine (FIG. 9A) suggesting utilization of carnitine for esterification of [$^{18}$F]FDMP. Unlabeled [$^{19}$F]FDMP was also rapidly taken up by BT474 cells, detected by mass spectrometry (FIG. 9B). At the higher probe concentrations used (500 μM in medium), we confirmed the presence of intracellular [$^{19}$F]FDMP; however, no other metabolites were observed. The presence of a coenzyme A (CoA) derivative of [$^{19}$F]FDMP could not be ruled out, since in control experiments with [$^{19}$F]fluroacetate [$^{19}$F]FAC), only the parent compound and [$^{19}$F]fluorocitrate were observed (FIG. 10), which implies conversion via fluoroacetyl-CoA. [$^{19}$F]FAC caused negative feedback inhibition in cells (significant increase in citrate and cis-aconitate, together with significant decrease in alpha-ketoglutarate due to inhibition of aconitase; FIG. 10).

Measurements In Vivo

Figure 11:
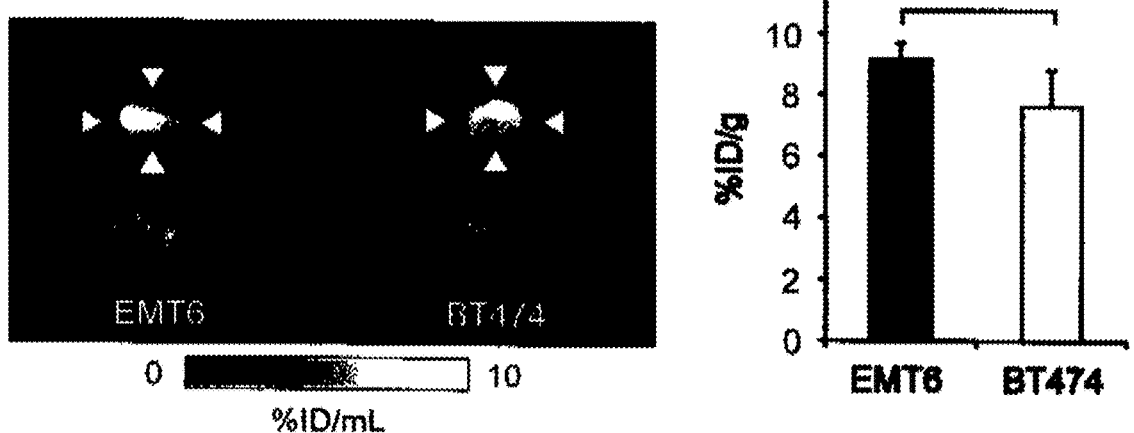
FIG. 11. Comparison between [$^{18}$F]FDMP uptake in murine EMT6 and human BT474 breast tumours 60 min post radiotracer injection (n=4 mice per group).

We next evaluated [$^{18}$F]FDMP for in vivo tumour imaging. Substantial [$^{18}$F]FDMP tumour localization was measured by PET in EMT6 murine breast adenocarcinoma xenografts, clearly visible above background normal tissue (FIG. 7). High [$^{18}$F]FDMP uptake was also observed in the bladder, kidney and salivary glands (FIG. 1). Similar to in vitro cell uptake, tumour-associated radioactivity linearly increased over the initial 30 min post injection to 9.3±1.0% ID/g, followed by stable retention in the tumour up to 120 min post radiotracer injection (9.8±2.0% ID/g). By 180 min, tumour-associated [$^{18}$F]FDHP reduced 36% to 6.3±0.7% ID/g. [$^{18}$F]FDMP pharmacokinetics were characterized by initial liver uptake, followed by rapid clearance, with the urinary tract being the primary route of excretion, determined both by biodistribution (FIG. 2) and from tissue TACs derived from dynamic imaging studies (FIG. 6). Furthermore, tumour radioactivity was comparable for both the murine and human breast adenocarcinoma tumour models, reaching 9.1±0.5% ID/g and 7.6±1.2% ID/g at 60 min post injection in EMT6 and BT474 tumours, respectively (FIG. 11).

Radiotracer Stability In Vivo

To confirm that tissue-associated radioactivity corresponded with parent [$^{18}$F]FDMP, rather than undesired degradation products, [$^{18}$F]FDMP stability was tested in tissues. [$^{18}$F]FDMP showed good stability in plasma, liver and heart at 30 min post injection, with only peaks of the parent compound detectable by radioHPLC (FIG. 5). In the urine, the parent peak was the dominant fraction at 30 min (61.8±6.6% radioactivity), with an additional unidentified metabolite peak observed at 6.5 min (37.3±6.0% radioactivity).

Comparison of [$^{18}$F]FDMP to [$^{18}$F]FDG for Tumour Detection

Given the promising [$^{18}$F]FDMP uptake in EMT6 tumours, dynamic [$^{18}$F]FDMP PET imaging was performed over 60 min and compared to the gold-standard PET tracer for tumour diagnosis, [$^{18}$F]FDG; the same scanner was used for both radiotracers. High tumour uptake was detected by PET for both [$^{18}$F]FDMP and [$^{18}$F]FDG in EMT6 tumours, illustrated in 50-60 min images (FIG. 7). In contrast, DU145 prostate adenocarcinoma tumours were clearly discernable by [$^{18}$F]FDMP PET, whereas tumour-associated radioactivity with [$^{18}$F]FDG was not visible above background in 50-60 min static scans (FIG. 12). For EMT6 tumours, tumour to whole body normalized uptake reached 1.02±0.16 NUV at 60 min for [$^{18}$F]FDG, compared to 1.15±0.13 for [$^{18}$F]FDMP (FIG. 12B; P=0.08; n=4-6). Semi-quantitative imaging parameters derived from the tumour TAC also could not differentiate between these two tracers (FIG. 7). Although lower than for EMT6 tumours, [$^{18}$F]FDMP tumour uptake was 54% higher than [$^{18}$F]FDG in DU145 prostate tumours, at 0.73±0.07 and 0.47±0.09 NUV, respectively (FIG. 12B; P=0.002; n=4-5).

Given that [$^{18}$F]FDMP passes the blood brain barrier, shown by both gamma counting and by dynamic PET (FIG. 2 and FIG. 6, respectively), we next tested the potential to use [$^{18}$F]FDMP to detect tumours of the brain, comparing uptake values to [$^{18}$F]FDG using the well-characterized U87 glioma model. In these human-derived xenografts, similarly high [$^{18}$F]FDMP and [$^{18}$F]FDG tumour uptake was measured 60 min post-radiotracer injection, at 9.35±1.0% ID/g and 11.0±1.1% ID/g, respectively (FIG. 8; P=0.07; n=4). Although tumour uptake was similarly high for the two radiotracers, [$^{18}$F]FDMP provided significantly higher tumour/brain ratio of 2.5, compared to just 1.3 with [$^{18}$F]FDG (P=0.001; n=4; FIG. 8).

Figure 14:
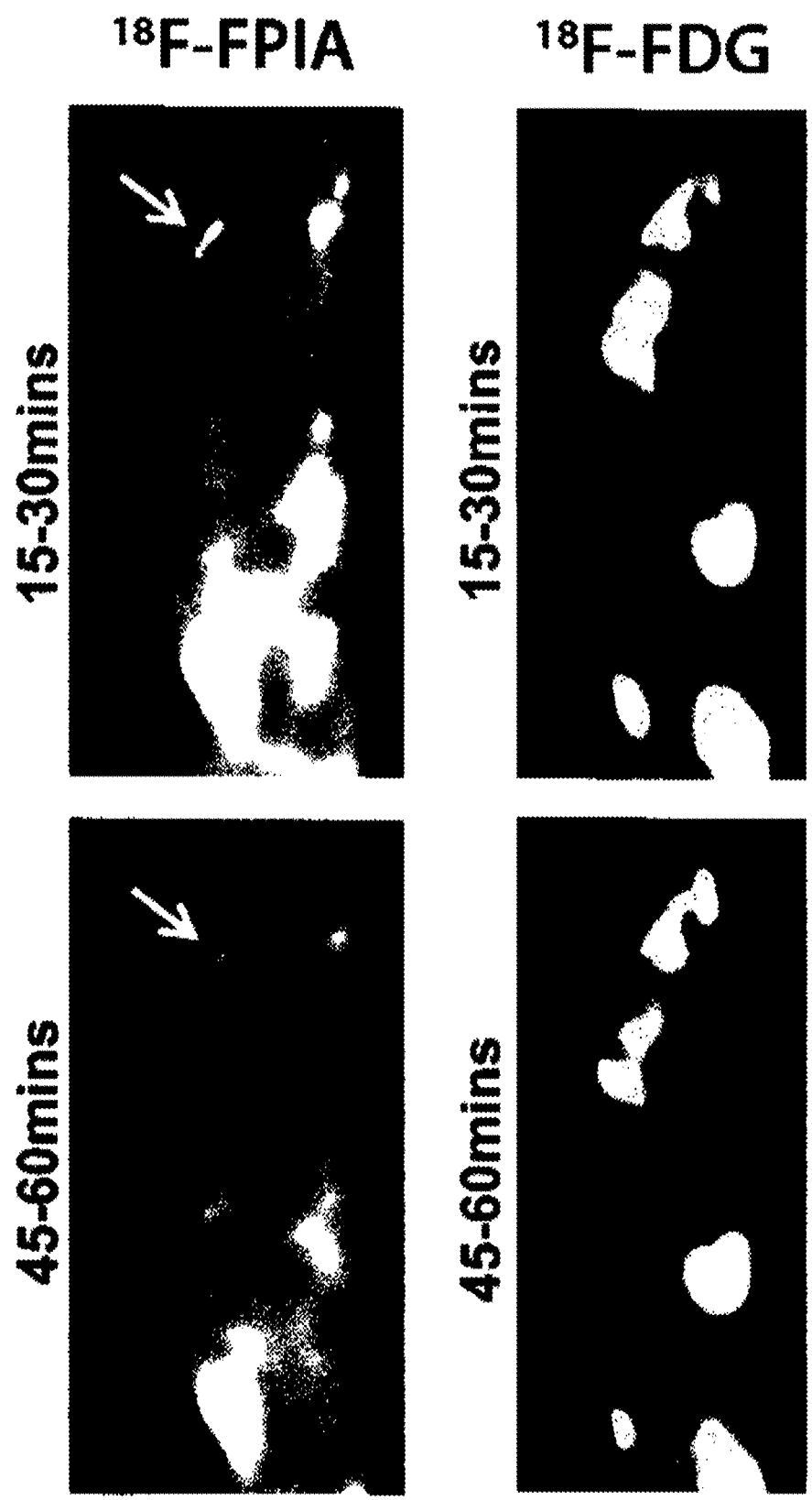
FIG. 14. [$^{18}$F]FDMP and [$^{18}$F]FDG uptake in an orthotopic U87 brain tumour model. PET images were acquired 15-30 min and 45-60 min post radiotracer injection 6 weeks after intracranial injection of U87 glioma cells. White arrows indicate the tumour.

[$^{18}$F]FDMP and [$^{18}$F]FDG uptake in an orthotopic U87 brain tumour model was analysed (FIG. 14). Comparison of the PET images, which were acquired 15-30 min and 45-60 min post radiotracer injection, show that a good staining of the U87 tumour was visible with FDMP tracer. These data demonstrate that [$^{18}$F]FDMP performs well as a tracer for brain tumour modelling in vivo. The background is very low, so good staining is achieved. The tracer showed a better uptake and staining in PET images at an earlier timepoint (15-30 min).

Figure 13:
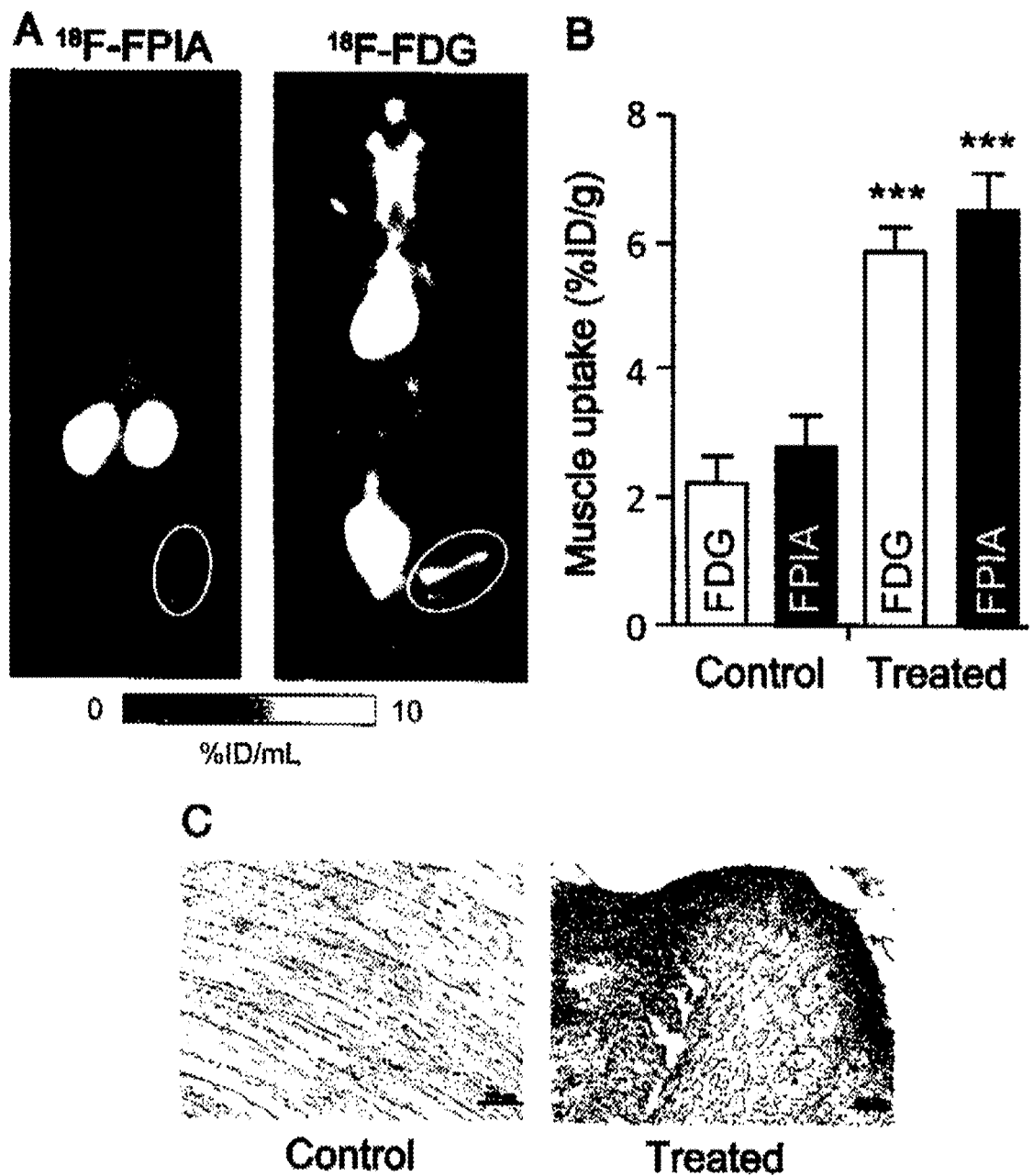
FIG. 13. [$^{18}$F]FDMP and [$^{18}$F]FDG uptake in an aseptic inflammation model. (A) Representative coronal PET images (30-60 summed frames) for [$^{18}$F]FDMP and [$^{18}$F]FDG. Turpentine-induced inflammatory tissue is circled in white. (B) [$^{18}$F]FDMP and [$^{18}$F]FDG biodistribution of the turpentine-treated and control, untreated posterior thigh muscle. Mean±SD (n=3-4). *** P<0.001. (C) Immunohistochemistry analysis by H&E staining in control and turpentine-treated muscle. Representative photographic images of H&E-stained sections were acquired at 200× magnification. Scale bar=100 µm.

Inflammatory cells are known to display both elevated glycolysis and fatty acid oxidation.[27] Given this, we explored [$^{18}$F]FDMP and known ability of [$^{18}$F]FDG to image this condition using an aseptic inflammation model. Both [$^{18}$F]FDMP and [$^{18}$F]FDG accumulated in chemically-induced inflammatory tissues, at 6.53±1.13% ID/g and 5.86±0.68% ID/g, respectively (FIG. 13). There was no significant difference between inflammation-to-muscle ratios for [$^{18}$F]FDMP (2.36) and [$^{18}$F]FDG (2.66).

Comparison of [$^{18}$F]FDMP to [$^{18}$F]FPA

[$^{18}$F]2-fluoropropionic acid ([$^{18}$F]FPA) has described as a potentially useful PET tracer by Pillarsetty et al.[28] The data presented herein show clear advantages for [$^{18}$F]FDMP when compared to [$^{18}$F]FPA. Data presented by Pillarsetty show an unfavourable tumour to blood ratio for [$^{18}$F]FPA. Essentially, the tumour uptake equals the blood distribution. This suggests that the pharmacokinetic data for [$^{18}$F]FPA are less favourable than for [$^{18}$F]FDMP. [$^{18}$F]FDMP's tumour to blood ratio is up to 2.32 after 60 minutes (FIG. 3) vs 1.03 for [$^{18}$F]FPA (Table 1 in reference 28).

Figure 4:
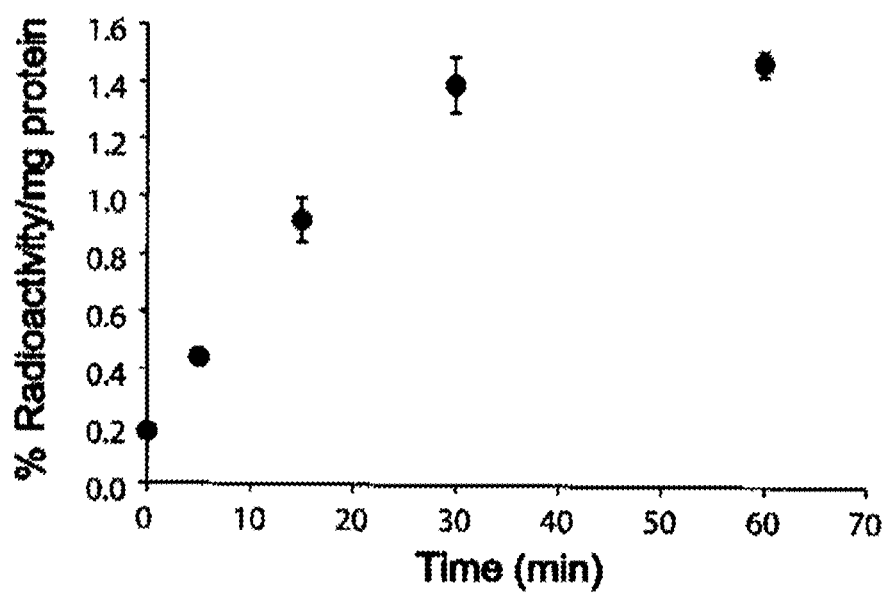
FIG. 4. Time course of [$^{18}$F]FDMP uptake in vitro in EMT6 murine breast adenocarcinoma cells. Mean values and SD are shown (n=3).

Furthermore, Pillarsetty et al. describe a tumour-to-brain ratio of 1.27 at 60 minutes post-injection for [$^{18}$F]FPA, this result being comparable to [$^{18}$F]FDG (ratio of 1.3 at 60 minutes as described herein). This is considerably worse than the ratio of 2.5 at 60 minutes post injection demonstrated by [$^{18}$F]FDMP (FIG. 8). In addition, [$^{18}$F]FPA lacks the 2,2-dialkyl substitution, predicting reduced metabolic stability leading to loss of the [$^{18}$F] label, exemplified by the bone uptake described by Pillarsetty et al. (FIG. 4 in reference 28).

Advantages of [$^{18}$F]FDMP

[$^{18}$F]FDMP is a preferred tracer compound of the invention. Although these advantages are not limited to [$^{18}$F] FDMP, and may be similarly exhibited by other compounds of the invention, [$^{18}$F]FDMP has been shown to compare favourably to other PET tracers as shown in the examples. Other tracer compounds for targeting tumours with high fatty acid synthesis include [$^{18}$F]choline and [$^{18}$F]fluoroacetate. [$^{18}$F]fluoroacetate is not as stable as [$^{18}$F]FDMP and therefore may be less interesting for applications such as dual-case PET/CT (2 imaging sessions over a course of time). [$^{18}$F]Choline is not recommended for imaging e.g. primary prostate tumours, due to its limited specificity. The results presented herein show that [$^{18}$F]FDMP, and other compounds of the invention, address an unmet need to provide a stable imaging agent which does not undergo de-labelling to lose its radionuclide label, and shows desirable specificity.

[$^{18}$F]FDMP was designed by the present inventors for the imaging of aberrant lipid metabolism associated with malignant transformation. The radiotracer showed high accumulation in breast, prostate and brain tumours, comparable or superior to that of [$^{18}$F]FDG. The lower normal brain uptake (hence inferred superior tumour-to-brain contrast) is a promising characteristic for brain tumour imaging.

Of course, it will be appreciated that the favourable pharmacokinetics demonstrated for [$^{18}$F]FDMP will also be displayed by differently labelled isotopologue forms of FDMP, for example, [1-$^{13}$C][$^{18}$F]FDMP and [1-$^{13}$C]FDMP.

REFERENCES

The following references are expressly incorporated by reference for all purposes in their entirety.
(1) http://info.cancerresearchuk.org/cancerstats/types/prostate/incidence/.
(2) Hou, A. H.; Sullivan, K. F.; Crawford, E. D. *Current opinion in urology* 2009, 19, 283.
(3) Wahl, R.; Harney, J.; Hutchins, G.; Grossman, H. *J. Urol.* 1991, 146, 1470.
(4) Waniewski, R. A.; Martin, D. L. *J Neurosci* 1998, 18, 5225.
(5) Wolfe, R. R.; Jahoor, F. *Am J Clin Nutr* 1990, 51, 248.
(6) Kuhajda, F. P. *Nutrition* 2000, 16, 202.
(7) Kridel, S. J.; Lowther, W. T.; Pemble, C. W. *Expert Opin Inv Drug* 2007, 16, 1817.
(8) Ponde, D. E.; Dence, C. S.; Oyama, N.; Kim, J.; Tai, Y.-C.; Laforest, R.; Siegel, B. A.; Welch, M. J. *Journal of Nuclear Medicine* 2007, 48, 420.
(9) a). Even-Sapir, E.; Mishani, E.; Flusser, G.; Metser, U. *Semin Nucl Med* 2007, 37, 462; b) Lindhe, Ö.; Sun A.; Ulin, J.; Rahman, O.; Långström, B; Sorensen, J, 2009; *European Journal of Nuclear Medicine*, 36, 1453.
(10) Tecle, B.; Casida, J. E. *Chemical Research in Toxicology* 1989, 2, 429.
(11) Lauble, H.; Kennedy, M. C.; Emptage, M. H.; Beinert, H.; Stout, C. D. *Proceedings of the National Academy of Sciences* 1996, 93, 13699.
(12) Villafranca, J. J.; Platus, E. *Biochemical and biophysical research communications* 1973, 55, 1197.
(13) Ardenkjaer-Larsen, J. H.; Fridlund, B; Gram, A; Hansson, G; Hansson, L; Lerche, M. H.; Servin, R.; Thaning, M.; Golman, K.; *Proc. Natl. Acad. Sci. USA* 2003, 100, 10158.
(14) Pardridge, W. M.; *Am. Physiol. Soc.* 1983, 63, 1481.
(15) Jensen, P. R.; Peitersen, T.; Karlsson, M.; *J. Biol. Chem.* 2009, 284, 36077.
(16) Wiegand, G.; Remington, S. *J. Annu Rev Biophys Biophys Chem* 1986, 15, 97.
(17) Brass E P and Hoppel C L (1980) Relationship between acid-soluble carnitine and coenzyme A pools in vivo. The Biochemical journal 190: 495-504.
(18) Ollrich K J, Rumrich G and Kloss S (1982) Reabsorption of Monocarboxylic Acids in the Proximal Tubule of the Rat-Kidney 0.1. Transport Kinetics of D-Lactate, Na+-Dependence, Ph-Dependence and Effect of Inhibitors. Pflug Arch Eur J Phy 395: 212-219.
(19) Diep Q N, Brors O and Bohmer T (1995) Formation of pivaloylcarnitine in isolated rat heart cells. Biochimica et biophysica acta 1259: 161-165.
(20) Rebouche C J (2004) Kinetics, pharmacokinetics, and regulation of L-carnitine and acetyl-L-carnitine metabolism. Annals of the New York Academy of Sciences 1033: 30-41.
(21) Eaton S, Fukumoto K, Stefanutti G, Spitz L, Zammit V A, et al. (2003) Myocardial carnitine palmitoyltransferase I as a target for oxidative modification in inflammation and sepsis. Biochem Soc Trans 31: 1133-1136.
(22) Workman P, Aboagye E O, Balkwill F, Balmain A, Bruder G, et al. (2010) Guidelines for the welfare and use of animals in cancer research. Br J Cancer 102: 1555-1577.
(23) Witney T H, Carroll L, Alam I S, Chandrashekran A, Nguyen Q D, et al. (2014) A novel radiotracer to image glycogen metabolism in tumours by positron emission tomography. Cancer research 74: 1319-1328.
(24) Smith G, Zhao Y, Leyton J, Shan B, Nguyen Q D, et al. (2011) Radiosynthesis and pre-clinical evaluation of [(18) F]fluoro-[1,2-(2)H(4)]choline. Nucl Med Biol 38: 39-51.
(25) Bieber L L. (1988) Carnitine. Annu Rev Biochem. 57: 261-283.
(26) Todesco L, Bodmer M, Vonwil K, Haussinger D, Krahenbuhl S. (2009) Interaction between pivaloylcarnitine and L-carnitine transport into L6 cells overexpressing hOCTN2. Chem-Biol Interact. 180(3): 472-477.
(27) O'Neill L A and Hardie D G (2013) Metabolism of inflammation limited by AMPK and pseudo-starvation. Nature 493: 346-355.
(28) (a) Pillarsetty N, Punzalan B, and Larson S M (2009) 18F-FPA as PET tracer for prostate cancer. J. Nucl. Med. 50: 1709-1714; (b) WO2010/005697 A2.

The invention claimed is:

1. A composition comprising a tracer, wherein the tracer is a labelled carboxylic acid or the corresponding carboxylate of Formula (I)

wherein
$C^L$ is selected from [$^{13}$C]carbon or [$^{11}$C]carbon;
n is 1, 2, or 3;
$R^1$ and $R^2$ are independently $C_{1-4}$-alkyl;
$R^3$ and $R^4$ are independently H or F; and
$R^5$ is F, Cl, Br, I, or $NH_2$.

2. The composition of claim 1, wherein $C^L$ is [$^{13}$C]carbon.

3. The composition of claim 1, wherein $R^3$ and $R^4$ are both hydrogen.

4. The composition of claim 1, wherein n is 1.

5. The composition of claim 1, wherein $R^1$ and $R^2$ are both methyl.

6. The composition of claim 1, wherein the tracer is a labelled carboxylic acid or the corresponding carboxylate of formula (Ia):

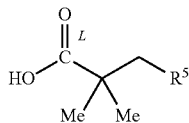

wherein
$C^L$ is [$^{13}$C]carbon or [$^{11}$C]carbon and
$R^5$ is F, Cl, Br, I, or $NH_2$.

7. The composition of claim 6 wherein $C^L$ is [$^{13}$C]carbon.

8. The composition of claim 6 wherein $R^5$ is fluorine.

9. The composition of claim 1, wherein the carboxylic acid is [1-$^{13}$C]3-fluoro-2,2-dimethylpropanoic acid.

10. A composition comprising a tracer, wherein the tracer is a labelled carboxylic acid or the corresponding carboxylate of Formula (I)

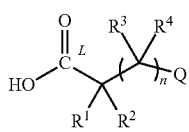

wherein
$C^L$ is selected from [$^{13}$C]carbon, [$^{12}$C]carbon, or [$^{11}$C]carbon;
n is 1, 2, or 3;
$R^1$ and $R^2$ are independently $C_{1-4}$-alkyl;
$R^3$ and $R^4$ are independently H or F; and
Q is selected from [$^{13}$C] and [$^{15}$N].

11. The composition of claim 10, wherein the tracer is a labelled carboxylic acid or the corresponding carboxylate of formula (Ia):

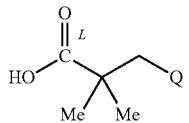

wherein $C^L$ is selected from [$^{13}$C]carbon, [$^{12}$C]carbon, or [$^{11}$C]carbon; and
Q is selected from [$^{13}$C] and [$^{15}$N].

12. A method of imaging for diagnosing a condition in a subject, wherein the method comprises:

hyperpolarizing the tracer compound of the composition according to claim 1 by dynamic nuclear polarization (DNP);
(ii) administering the composition to the subject;
(iii) collecting magnetic resonance spectroscopy (MRS) or magnetic resonance imaging (MRI) data associated with the hyperpolarized tracer compound;
(iv) acquiring at least one image by magnetic resonance spectroscopy (MRS) or magnetic resonance imaging (MRI); and
(v) diagnosing the condition in the subject using the image.

13. The method of diagnosis of claim 12, wherein the condition is a lesion or diseased tissue that has an altered lipid turnover compared to levels in healthy tissue of the same organ or origin.

14. The method of claim 12, wherein the condition is a tumor.

15. The method of claim 14 wherein the tumor is a hypoxic tumor or a tumor having perturbed carnitine metabolism.

16. The method of claim 12, wherein the condition is breast, brain, prostate, colon, esophageal, lung, pancreatic or liver cancer; or wherein the condition is metastasis, Alzheimer's disease, multiple sclerosis, a heart-related disease or disorder, or a genetic/epigenetic disease of lipid metabolism.

17. A method of imaging for diagnosing a condition in a subject, wherein the method comprises:

hyperpolarizing the tracer compound of the composition according to claim 10 by dynamic nuclear polarization (DNP);
(ii) administering the composition to the subject;
(iii) collecting magnetic resonance spectroscopy (MRS) or magnetic resonance imaging (MRI) data associated with the hyperpolarized tracer compound;
(iv) acquiring at least one image by magnetic resonance spectroscopy (MRS) or magnetic resonance imaging (MRI); and
(v) diagnosing the condition in the subject using the image.

18. The method of diagnosis of claim 17, wherein the condition is a lesion or diseased tissue that has an altered lipid turnover compared to levels in healthy tissue of the same organ or origin.

19. The method of claim 17, wherein the condition is a tumor.

20. The method of claim 19 wherein the tumor is a hypoxic tumor or a tumor having perturbed carnitine metabolism.

21. The method of claim 17, wherein the condition is breast, brain, prostate, colon, esophageal, lung, pancreatic or liver cancer; or wherein the condition is metastasis, Alzheimer's disease, multiple sclerosis, a heart-related disease or disorder, or a genetic/epigenetic disease of lipid metabolism.

22. A method of imaging for diagnosing a condition in a subject, wherein the method comprises:
(i) administering the composition according to claim 1 to the subject;
(ii) detecting gamma rays emitted, either directly or indirectly, by the tracer;
(iii) acquiring at least one image associated with the gamma rays emitted by the tracer; and
(iv) diagnosing the condition in the subject using the image.

23. The method of diagnosis of claim 22, wherein the condition is a lesion or diseased tissue that has an altered lipid turnover compared to levels in healthy tissue of the same organ or origin.

24. The method of claim 22, wherein the condition is a tumor.

25. The method of claim 24 wherein the tumor is a hypoxic tumor or a tumor having perturbed carnitine metabolism.

26. The method of claim 22, wherein the condition is breast, brain, prostate, colon, esophageal, lung, pancreatic or liver cancer; or wherein the condition is metastasis, Alzheimer's disease, multiple sclerosis, a heart-related disease or disorder, or a genetic/epigenetic disease of lipid metabolism.

27. The composition of claim 1, wherein $R^5$ is F, CL, Br, or I.

* * * * *